US008337863B2

(12) United States Patent
Gustafson et al.

(10) Patent No.: US 8,337,863 B2
(45) Date of Patent: Dec. 25, 2012

(54) ANTI-SEPSIS CONJUGATE VACCINE

(75) Inventors: Gary L. Gustafson, Missoula, MT (US); Dan C. DeBorde, Missoula, MT (US)

(73) Assignee: EndoBiologics, Incorporated, Missoula, MT (US)

( * ) Notice: Subject to any disclaimer, the term of this patent is extended or adjusted under 35 U.S.C. 154(b) by 0 days.

(21) Appl. No.: 13/366,490

(22) Filed: Feb. 6, 2012

(65) Prior Publication Data

US 2012/0301500 A1 Nov. 29, 2012

Related U.S. Application Data

(63) Continuation of application No. 12/785,312, filed on May 21, 2010, now Pat. No. 8,128,942, which is a continuation of application No. 11/274,847, filed on Nov. 15, 2005, now Pat. No. 7,749,511, which is a continuation-in-part of application No. 10/271,253, filed on Oct. 15, 2002, now Pat. No. 7,014,857, which is a continuation of application No. PCT/US01/12417, filed on Apr. 17, 2001.

(60) Provisional application No. 60/197,739, filed on Apr. 18, 2000, provisional application No. 60/231,875, filed on Sep. 12, 2000.

(51) Int. Cl.
| A61K 39/02 | (2006.01) |
| A61K 39/108 | (2006.01) |
| A61K 39/385 | (2006.01) |
| A61K 31/70 | (2006.01) |
| C07H 1/00 | (2006.01) |

(52) U.S. Cl. ............... 424/260.1; 424/234.1; 424/184.1; 424/197.11; 424/194.1; 514/23; 536/123.1

(58) Field of Classification Search .................. None
See application file for complete search history.

(56) References Cited

U.S. PATENT DOCUMENTS

| 4,771,127 | A | 9/1988 | Cryz et al. |
| 5,306,492 | A | 4/1994 | Porro |
| 5,370,872 | A | 12/1994 | Cryz et al. |
| 5,445,817 | A | 8/1995 | Schneerson et al. |
| 5,573,916 | A | 11/1996 | Cheronic et al. |
| 5,679,654 | A | 10/1997 | Tzianabos et al. |
| 5,700,784 | A | 12/1997 | Shinojima et al. |
| 5,736,146 | A | 4/1998 | Cohen et al. |
| 5,739,313 | A | 4/1998 | Collins et al. |
| 5,785,973 | A | 7/1998 | Bixler et al. |
| 5,866,132 | A | 2/1999 | Malcolm |
| 5,869,058 | A | 2/1999 | Cohen et al. |
| 6,531,131 | B1 | 3/2003 | Gu et al. |
| 6,645,503 | B1 | 11/2003 | Arumugham et al. |
| 7,014,857 | B2 | 3/2006 | Gustafson et al. |
| 7,749,511 | B2 | 7/2010 | Gustafson et al. |
| 2005/0147624 | A1 | 7/2005 | Jennings et al. |
| 2006/0073163 | A1 | 4/2006 | Gustafson et al. |
| 2011/0027307 | A1 | 2/2011 | Gustafson et al. |

FOREIGN PATENT DOCUMENTS

| EP | 0941738 A1 | 9/1999 |
| WO | WO-93/03765 A1 | 3/1993 |
| WO | WO-93/13797 A2 | 7/1993 |
| WO | WO-94/05325 A1 | 3/1994 |
| WO | WO-02/45708 A2 | 6/2002 |
| WO | WO-2007/059115 A1 | 5/2007 |
| WO | WO-2007/092451 A2 | 8/2007 |

OTHER PUBLICATIONS

*The Webster's II New Riverside University Dictionary*, Definition of "prevent", The Riverside Publishing Company, (1984), p. 933.
*Illustrated Stedman's Medical Dictionary*, 24th Edition, Definition of "infect", Williams & Wilkins, Baltimore, (1982), p. 707.
"U.S. Appl. No. 10/271,253, Non Final Office Action mailed Mar. 22, 2005", 10 pgs.
"U.S. Appl. No. 10/271,253, Non Final Office Action mailed Nov. 16, 2004", 9 pgs.
"U.S. Appl. No. 10/271,253, Notice of Allowance mailed Aug. 25, 2005", 8 pgs.
"U.S. Appl. No. 10/271,253, Preliminary Amendment filed Oct. 15, 2002", 1 pg.
"U.S. Appl. No. 10/271,253, Response filed Jun. 10, 2005 to Non Final Office Action mailed Mar. 22, 2005", 7 pgs.
"U.S. Appl. No. 10/271,253, Response filed Aug. 31, 2004 to Restriction Requirement mailed May 19, 2004", 2 pgs.
"U.S. Appl. No. 10/271,253, Response flied Dec. 9, 2004 to Non Final Office Action mailed Nov. 16, 2004", 8 pgs.
"U.S. Appl. No. 10/271,253, Restriction Requirement mailed May 19, 2004", 5 pgs.
"U.S. Appl. No. 11/274,847, Final Office Action mailed Nov. 10, 2008", 9 pgs.
"U.S. Appl. No. 11/274,847, Non-Final Office Action mailed May 7, 2008", 7 pgs.
"U.S. Appl. No. 11/274,847, Non-Final Office Action mailed May 27, 2009", 7 pgs.
"U.S. Appl. No. 11/274,847, Notice of Allowability with Interview Summary and Examiner's Amendment mailed Jan. 27, 2010", 7 pgs.
"U.S. Appl. No. 11/274,847, Notice of Allowance mailed Feb. 23, 2010", 9 pgs.
"U.S. Appl. No. 11/274,847, Preliminary Amendment filed Oct. 16, 2007", 10 pgs.
"U.S. Appl. No. 11/274,847, Response filed Feb. 5, 2008 to Restriction Requirement mailed Dec. 27, 2007", 2 pgs.
"U.S. Appl. No. 11/274,847, Response filed Mar. 10, 2009 to Final Office Action mailed Nov. 10, 2008", 9 pgs.
"U.S. Appl. No. 11/274,847, Response filed Aug. 7, 2008 to Non-Final Office Action mailed May 7, 2008", 12 pgs.
"U.S. Appl. No. 11/274,847, Response filed Sep. 28, 2009 to Non Final Office Action mailed May 27, 2009", 8 pgs.

(Continued)

*Primary Examiner* — S. Devi
(74) *Attorney, Agent, or Firm* — Schwegman Lundberg & Woessner, P.A.

(57) ABSTRACT

The present invention provides an immunogenic conjugate comprising biologically deacylated gram-negative bacterial moieties linked to *D. discoideum* proteinase 1, as well as novel subunits thereof, and methods of making and using the conjugates in vaccines to treat sepsis and other infectious complications.

7 Claims, 5 Drawing Sheets

OTHER PUBLICATIONS

"U.S. Appl. No. 11/274,847, Restriction Requirement mailed Dec. 27, 2007", 7 pgs.

"U.S. Appl. No. 12/785,312, Non Final Office Action mailed Mar. 17, 2011", 11 pgs.

"U.S. Appl. No. 12/785,312, Notice of Allowance mailed Oct. 21, 2011", (w/Interview Summary), 10 pgs.

"U.S. Appl. No. 12/785,312, Preliminary Amendment mailed Aug. 4, 2010", 4 pgs.

"U.S. Appl. No. 12/785,312, Response filed Sep. 19, 2011 to Non Final Office Action mailed Mar. 17, 2011", 10 pgs.

"U.S. Appl. No. 12/785,312, Response filed Dec. 22, 2010 to Restriction Requirement mailed Dec. 2, 2010", 5 pgs.

"U.S. Appl. No. 12/785,312, Restriction Requirement mailed Dec. 2, 2010", 6 pgs.

"Increase in National Hospital Discharge Survey Rates for Septicemia—United States, 1979-1987", Morbidity and Mortality Weekly Report, 39(1), (Jan. 12, 1990).

"International Search Report for Application No. PCT/US06/44161", (Mar. 21, 2007).

"Outbreaks of *Salmonella* Serotype Enteritidis Infection Associated With Eating Raw or Undercooked Shell Eggs—United States, 1996-1998". *Morbidity and Mortality Weekly Report*, 49(4), (Feb. 4, 2000), 73-79.

"Outbreaks of *Salmonella* Serotype Enteritidis Infection Associated with Eating Raw Undercooked Shell Eggs—United States, 1996-1998", *CDC, MMWR, Morbidity and Mortality Weekly Report*, (2000), 1132-1134.

Abramson, S., et al., "*Salmonella* Bacteremia in Systematic Lupus Erythematosus", *Arthritis and Rheumatism*, 28(1), (1985), 75-79.

Agarwal, A. K., et al., "Ribosomal Protein Gene Expression is Cell Type Specific During Development in *Dictyostelium discoideum*", *Differentiation*, 65, (1999), 73-88.

Ames, B., "Assay of Inorganic Phosphate, Total Phosphate and Phosphatases", *In: Methods in Enzymology, Vol. VIII—Complex Carbohydrates*, (Neufeld, E. F., Editors, et al, Academic Press, Inc.), (1966), 115-118.

Ashkenazi, S., et al., "Safety and Immunogenicity of *Shigella sonnei* and *Shigella flexneri* 2a O-Specific Polysaccharide Conjugates in Children", *The Journal of Infectious Diseases*, 179, (1999), 1565-1568.

Ashwell, G., et al., "A Colorimetric Procedure for the Determination of N-Acetylated-3-Amino Hexoses", *Archives of Biochemistry and Biophysics*, 112, (1965), 648-652.

Bahrami, S., et al., "Monoclonal antibody to endotoxin attenuates hemorrhage-induced lung injury and mortality in rats", *Critical Care Med.*, 25(6), (Jun. 1997), 1030-1036.

Bailat, S., et al., "Similarities and Disparities between Core-Specific and O-Side-Chain-Specific Antipopolysaccharide Monoclonal Anitbodies in Models of Endotoxemia and Bacteremia in Mice", *Infection and Immunity*, 65(2), (Feb. 1997), 811-814.

Barriere. S., et al., "An overview of mortality risk prediction in sepsis", *Critical Care Medicine*, 23(2), (1995), pp. 376-378, 383-388, 393.

Baumgartner, J. D., et al., "Antibodies to Lipopolysacchardides after Immununization of Humans with the Rough Mutant *Escherichia coil* J5", *The Journal of Infectious Diseases*, 163(4), (1991), 769-772.

Baumgartner, J.-D., et al., "Immunology of Endotoxemia and Septicemia", *Immunobiology*, 187, (1993). 464-477.

Bergquist, C., et al., "Anticarrier Immunity Suppresses the Antibody Response to Polysaccharide Antigens after Intranasal Immunization with the Polysaccharide-Protein Conjugate", *Injection and Immunity*, 65(5), (May 1997), 1579-1583.

Bhattacharjee, A., et al., "A Noncovalent Complex Vaccine Prepared with Detoxified *Escherichia coli* J5 (Rc Chemotype) Lipopolysaccharide and *Neisseria meningitidis* Group B Outer Membrane Protein Produces Protective Antibodies against Gram-Negative Bacteremia", *The Journal of Infectious Diseases*, 173, (1996), 1157-1163.

Bhattacharjee, A., et al., "Affinity-Purified *Escherichia coil* J5 Lipopolysaccharide-Specific IgG Protects Neutropenic Rats against Gram-Negative Bacterial Sepsis", *The Journal of Infectious Diseases*, 170, (1994), 622-629.

Blanqué, R., et al., "Hypothermia as an Indicator of the Acute Effects of Lipopolysaccharides: Comparison with Serum Levels of IL1β, IL6 and TNFα", *Gen. Pharmac.*, 27(6), (1996), 973-977.

Bone, R. C., et al., "A Controlled Clinical Trial of High-Does Methylprednisolone in the Treatment of Severe Sepsis and Septic Shock", *The New England Journal of Medicine*, 317(11), (1987), 653-658.

Bone, R., et al., "The Pathogenesis of Sepsis", *Annals of Internal Medicine*, 115, (1991), 457-469.

Braude, A., et al., "Antibody to Cell Wall Glycolipid of Gram-Negative Bacteria: Induction of Immunity to Bacteremia and Endotoxemia", *The Journal of Infectious Diseases*, 136, (1977), S167-S173.

Braude, A., et al., "Treatment and Prevention of Intravascular Coagulation with Antiserum Endotoxin", *The Journal of Infectious Diseases*, 128, (1973), S157-S163.

Bruins, S. C., et al., "Immunization with R Mutants of *Salmonella minnesota*", *Infection and Immunity*, 17(1), (1977), 16-20.

Chamberland, S., et al., "Antibiotic Susceptibility Profiles of 941 Gram-Negative Bacteria Isolated from Septicemic Patients Throughout Canada", *Clinical Infectious Diseases*, 15, (1992), 615-628.

Clemmer, T. P., et al., "Hypothermia in the Sepsis Syndrome and Clinical Outcome", *Critcal Care Medicine*, 20(10), (1992), 1395-1401.

Cohen, D., et al., "Double-Blind Vaccine-Controlled Randomised Efficacy Trial of an Investigational *Shigella sonnei* Conjugate Vaccine in Young Adults", *Lancet*, 349, (1997), 155-159.

Cohen, D., et al., "Safety and Immunogenicity of Investigational *Shigella* Conjugate Vaccines in Israeli Volunteers", *Infection and Immunity*, 64(10), (1996), 4074-4077.

Cryz, S. J., et al., "Immunization of Cystic Fibrosis Patients with a *Pseudomona aeruginosa* O-Polysaaccharide-Toxin A Conjugate Vaccine", *Behring Institute Mitteilungen*, 98, (Feb. 1997), 345-349.

Di John, D., et al., "Effect of Priming with the Carrier on Response to Conjugate Vaccine", *The Lancet*, (1989), 1415-1418.

Di Padova, F., et al., "A Broadly Cross-Protective Monoclonal Antibody Binding to *Escherichia coli* and *Salmonella* Lipopolysaccharides", *Infection and Immunity*, 61(9), (1993), 3863-3872.

Drewry, D. T., et al., "Release of Ethanolamine Pyrophosphate during Mild Acid Hydrolysis of the Lipopolysaccharide of *Pseudomonas aeruginosa*", *Eur. J. Biochem.* 21, (1971), 400-403.

Driscoll, D. M., et al., "Two Divergently Transcribed Genes of *Dictyostelium discoideum* are Cyclic AMP-inducible and Coregulated During Development", *Mol. Cell. Bio.*, 7, (1987), 4482-4489.

Estrin, Norman F, et al., "CTFA Cosmetic Ingredient Dictionary", © 1982 The Cosmetic, Toiletry and Fragrance Association, Inc., (1982), 3 pgs.

Finn, D., et al., "Antibodies that Recognize Phosphodiester-Linked α-N-Acetylglucosamine-1-Phosphate Residues", *Biochemical and Biophysical Research Communications*, 148(2), (1987), 834-837.

Flak, T., et al., "Muramyl Peptide Probes Derived from Tracheal Cytotoxin of *Bordetella pertussis*", *Analytical Biochemistry*, 264, (1998), 41-46.

Galanos, C., et al., "A New Method for the Extraction of R Lipopolysaccharides", *European J. Biochem.*, 9, (1969), 245-249.

Galanos, C., et al., "Biological Activities of Lipid A Complexed With Bovine-Serum Albumin", *Eur. J. Biochem.*, 31, (1972), 230-233.

Galanos, C., et al., "Mechanism of Endotoxin Shock and Endotoxin Hypertensitivity", *Immunobiol.*, 187, (1993), 346-356.

Galanos, C., et al., "Synthetic and natural *Escherichia coli* free lipid A express identical endotoxic activities", *Eur. J. Biochem.*, 148, (1985), 1-5.

Geerdes, H., et al., "Septicemia in 980 Patients at a University Hospital in Berlin: Prospective Studies During 4 Selected Years Between 1979 and 1989", *Clinical Infectious Diseases*, 15, (1992), 991-1002.

Good, T., et al., "Determination of Glucosamine and Galactosamine Using Borate Buffers for Modification of the Elson-Morgan and Morgan-Elson Reactions", *Analytical Biochemistry*, 9, (1964), 253-262.

Gu, X., et al., "Synthesis, Characterization, and Immunologic Properties of Detoxified Lipooligosaccharide from Nontypeable *Haemophilus influenza* Conjugated to Proteins", *Infection and Immunity*, 64(10), (1996), 4047-4053.

Gupta, R. K., et al., "Comparative Immunogenicity of Conjugates Composed of *Escherichia coli* O111 O-Specific Polysaccharide, Prepared by Treatment with Acetic Acid or Hydrazine, Bound to Tetanus Toxoid by Two Synthetic Schemes", *Infection and Immunity*, 63(8), (Aug. 1995), 2805-2810.

Gupta, R., et al., "Synthesis, Characterization, and Some Immunological Properties of Conjugates Composed of the Detoxified Lipopolysaccharide of *Vibrio cholerae* O1 Serotype Inaba Bound to Cholera Toxin", *Infection and Immunity*, 60(8), (1992), 3201-3208.

Gustafson, G., et al., "Monophosphoryl Lipid A as a Prophylactic for Sepsis and Septic Shock", *Bacterial Endotoxins: Lipopolysaccharides from Genes to Therapy*, (1995), 567-579.

Gustafson, G., et al., "Occurrence of N-acetylglucosamine-1-phosphate in proteinase I, from *Dictyostelium discoideum*", *Journal of Biolocical Chemistry*, 255(15), (Aug. 10, 1980), 7208-7210.

Gustafson, G. L., et al., "Purification and characterization of a proteinase from *Dictyostelium discoideum*", *Journal of Biological Chemistry*, 254(24), (Dec. 25, 1979), 12471-12478.

Hase, S., et al., "Isolation and Analysis of the Lipid A Backbone", *European Journal of Biochemistry*, 63, (1976), 101-107.

Herzenberg, L., et al., "Carrier-priming leads to hapten-specific suppression", *Nature*, 285, (1980), 664-667.

Hoffman, W., et al., "Endotoxin in Spetic Shock", *Anesth Analg.*, 77, (1993), 613-624.

Hu, W.-G., of al., "Enhancement of Clearance of Bacteria from Murine Lungs by Immunization with Detoxified Lipooligosaccharide from *Moraxella catarrhalis* Conjugated to Proteins", *Infection and Immunity*, 68(9), (2000), 4980-4985.

Jenne, N., et al., "Targeted Gene Disruption Reveals a Role for Vacuolin B in the Late Endocytic Pathway and Exocytosis", *Journal of Cell Science*, 111, (1998), 61-70.

Jennings, H. J., et al., "Conjugation of Meningococcal Lipopolysaccharide R-Type Oligosaccharides to Tetanus Toxoid as Route to a Potential Vaccine Against Group B *Neisseria menigitidis*", *Infection and Immunity*, 43(1), (1984), 407-412.

Johnson, K., et al., "Improved techniques for the preparation of bacterial lipopolysaccharides", *Can. J. Microbiol.*, 22, (1976), 29-34.

Kenne, L., et al., "Structural Studies of the O-Specific Side-Chains of the *Shigella sonnei* Phase I Lipopolysaccharide", *Carbohdyrate Research*, 78, (1980), 119-126.

Konadu, E., et al., "Investigational Vaccine for *Escherichia coli* O157: Phase 1 Study of O157 O-Specific Polysaccharide-*Pseudomonas aeruginosa* Recombinant Exoprotein A Conjugates in Adults", *Journal of Infectious Diseases*, 177, (1998), 383-387.

Konadu, E., et al, "Phase 1 and Phase 2 Studies of *Salmonella enterica* Serovar Paratyphi A O-Specific Polysaccharide-Tetanus Toxoid Conjugates in Adults, Teenagers, and 2- to 4-Year Old Children in Vietnam", *Infection and Immunity*, 68(3), (2000), 1529-1534.

Konadu, E., et al., "Preparation, Characterization, and Immunological Properties in Mice of *Escherichia coli* O157 O-Specific Polysaccharide-Protein Conjugate Vaccines", *Infection and Immunity*, 62(11), (1994), 5048-5054.

Kossaczka, Z., et al., "*Vibrio cholerae* O139 Conjugate Vaccines: Synthesis and Immunogenicity of *V. cholerae* O139 Capsular Polysaccharide Conjugates With Recombinate Diphtheria Toxin Mutant in Mice", *Infection and Immunity*, 68(9), (2000), 5037-5043.

Kreger, B., et al., "Gram-Negative Bacteremia", *The American Journal of Medicine*, 68, (1980), pp. 332-343.

Malchow, D., et al., "Polysaccharide in vegetativen und aggregationsreifen Amoben von *Dictyostelium discoideum*", (w/ English Abstract), *European J. Biochem.*, 2, (1967), 469-479.

Malchow, D., et al., "Polysaccharides in Vegetative and Aggregation-Competent Amoebae of *Dictyostelium discoideum* 2. Purification and Characterization of Amoeba-Degraded Bacterial Polyschharides", *European J. Biochem.*, 7 (2), (Jan. 1969), 239-246.

Marks, M., et al., "Induction of Immunity against Lethal *Haemophilus influenzae* Type b Infection by *Escherichia coli* Core Lipopolysaccharide", *J. Clin. Invest.*, 69, (1982), 742-749.

Masoud, H., et al., "General Strategy for Structural Analysis of the Oligosaccharide Region of Lipooligosaccharides. Structure of the Oligosaccharide Componet of *Pseudomonas aeruginosa* IATS Serotype 06 Mutant R5 Rough-Type Lipopolysaccharide", *Biochemistry*, 33, (1994), 10568-10578.

Masoud, H., et al., "Structural Elucidation of the Lipopolysaccharide Core Region of the O-Chain-Deficient Mutant Strain A28 from *Pseudomonas aeruginosa* Serotype 06 (International Antigenic Typing Scheme)", *J. Bacteriol.*, 177(23), (1995), 6718-6726.

Mehta, D., et al., "A lysosomal cysteine proteinase from *Dictyostelium discoideum* contains N-acetylglucosamine-1-phosphate bound to serine but not mannose-6-phosphate on N-linked oligosaccharides", *Journal of Biological Chemistry*, 271(18), (May 3, 1996), 10897-10903.

Moreno-Bueno, G., et al., "Isolation and Characterization of Casein Kinase I From *Dictyostelium discoideum*", *Biochem. J.*, 349, (2000), 527-537.

Muller-Loennies, S., et al., "Chemical Structure of the Core Region of *Escherichia coli* J-5 Lipopolysaccharide", *Eur. J. Biochem.*, 224, (1994), 751-760.

Muller-Loennies, S., et al., "Isoation and structural analysis of phosphorylated oligosaccharides obtained from *Escherichia coli* J-5 lipopolysaccharide", *European Journal of Biochemistry*, 260, (1999), 235-249.

Nadkarni, V., et al., "Directional Immobilization of Heparin onto Beaded Supports", *Analytical Biochemistry*, 222, (1994), 59-67.

Nnalue, N., et al., "The Disaccharide L-α-D-Heptose-7-L-α-D-Heptose1→ of the Inner Core Domain of *Salmonella* Lipopolysaccharide is Accessible to Antibody and is the Epitope of a Broadly Reactive Monoclonal Antibody", *The Journal of Immunology*, 149, (1992), 2722-2728.

North, M. J., "A Bacterial Factor Induces Changes in Cysteine Proteinase Forms in the Cellular Slime Mold *Dictyostelium discoideum*", *Biochem. J.*, 254, (1988), 269-275.

North, M. J., "Cysteine Proteinases of *Dictyostelium discoideum*: Changes Induced by a Factor Derived from Bacteria", *Biochem. Soc. Trans.*, 15, (1987), 1064-1065.

Ord, T., et al., "The Cysteine Proteinase Gene cprG in *Dictyostelium discoideum* Has a Serine-Rich Domain That Contains GlcNAc-1-P", *Archives of Biochemistry and Biophysics*, 339, (1997), 64-72.

Osborn, M., et al., "Studies on the Gram-Negative Cell Wall, I. Evidence for the Role of 2-Keto-3-Deoxyoctonate in the Lipopolysaccharide of *Salmonella typhimurium*", *Biochemistry*, 50, (1963), 499-506.

Pantosti, A., et al., "Immunochemical Characterization of Two Surface Polysaccharides of *Bacteroides fragilis*", *Infection and Immunity*, 59(6), (1991), 2075-2082.

Park, J., et al., "A Submicrodetermination of Glucose", *J. Biol. Chem*, 181, (1949), 149-151.

Plested, J. S., et al., "Conservation and Accessibility of an Inner Core Lipopolysaccharide Epitope of *Neisseria menignitidis*", *Infection and Immunity*, 67(10), (1990), 5417-5426.

Polotsky, V. Y, et al., "Comparison of Conjugates Composed of Lipopolysaccharides from *Shigella flexineri* Type 2a Detoxified by Two Methods and Bound to Tetanus Toxoid", *Infect. Immun*,62, (1994), 210-214.

Raabo, E., et al., "On the Enzymatic Determination of Blood Glucose", The Scandinavian *Journal of Clinical & Laboratory Investigation*, 12, (1960), 402-407.

Raetz, C., "Biochemistry of Endotoxins", *Annu. Rev. Biochem.*, 59, (1990), pp. 129-170.

Raetz, C. R.H., "Biochemistry of Endotoxins", *Annu. Rev. Biochem.*, 59, (1990), 129-170.

Renjifo, X., et al., "Carrier-Induced, Hapten-Specific Suppression: A Problem of Antigen Presentation?", *The Journal of Immunology*, (1998), 702-706.

Rietschel, E., et al., "Bacterial Endotoxin: Molecular Relationships Between Structure and Activity", *Infectious Disease Clinics of North America*, 5(4), (Dec. 1991), 753-779.

Rietschel, E. T., et al., "Bacterial Endotoxin: Molecular Relationships of Structure to Activity and Function", *FASEB Journal*, 8, (1994), 217-225.

Rietschel, E., et al., "Bacterial Endotoxins", *Scientific American*, 267, (Aug. 1992), 54-61.

Robbins, J. B., et al., "Hypothesis for Vaccine Development: Protective Immunity to Enteric Diseases Caused by Nontyphoidal *Salmonellae* and *Shigellae* May Be Conferred by Serum IgG Antibodies to the O-Specific Polysaccharide of Their Lipopolysaccharides", *Clinical Infectious Diseases*, 15, (1992), 346-361.

Robbins, J., et al., "Polysaccharide-Protein Conjugates: A New Generation of Vaccines", *The Journal of Infectious Diseases*, 161, (1990), 821-832.

Romanovsky, A. A., et al., "Endotoxin Shock: Thermoregulatory Mechanisms", *American Journal of Physiology*, 270, (1996), R693-R703.

Sadovskaya, I., et al., "Structural elucidation of the lipopolysaccharide core regions of the wild-type strain PAO1 and O-chain-deficient mutual strains. AK1401 and AK1012 from *Pseudomonas aeruginosa* serotype 05", *Eur. J. Biochem.*, 255, (1998), 673-684.

Schneerson, R. et al., "Serum Antibody Responses of Juvenile and Infant Rhesus Monkeys Injected with *Haemophilus influenzae* Type b and *Pneumococcus* Type 6A Capsular Polysaccharide-Protein Conjugates", *Infection and Immunity*, vol. 45(3). (Sep. 1984), 582-591.

Schutze, M., et al., "Carrier-Induced Epitopic Suppression is Initialed Through Clonal Dominance", *The Journal of Immunology*, 142, (1989), 2635-2640.

Schutze, M., et al., "Carrier-Induced Epitopic Suppression, A Major Issue for Future Synthetic Vaccines", *The Journal of Immunology*, 135, (1985), 2319-2322.

Seid, Jr., R. C., et al., "Enhanced Antigenicity and Immunogenicity of Gonococcal Pilus-Lipopolysaccharide Conjugates", *Proceedings of the Fourth International Symposium. American Society for Microbiology*, Washington, DC, (1985), 309-315.

Smith, R., et al., "Quantitation of Glycosaminoglycan Hexasamine Using 3-Methyl-2-Benzothiazolone Hydrazone Hydrochloride", *Analytical Biochemistry*, 98, (1979), 478-480.

Sriskandan, S., et al., "The Pathogenesis of Septic Shock", *Journal of Infection*, 30, (1995), pp. 201-206.

Suffredini, A., et al., "Current prospects for the treatment of clinical sepsis", *Critical Care Medicine*, 22, (1994), S12-S18.

Sun, J., et al., "Biological Activities of Antibodies Elicited by Lipooligosaccharide Based-Conjugate Vaccines of Nontypeable *Haemophilus influenzae* in an Otitis Media Model", *Vaccine*, 18, (2000), 1264-1272.

Taylor, D., et al., "Synthesis, Characterization, and Clinical Evaluation of Conjugate Vaccines Composed of the O-Specific Polysaccharides of *Shigella dysenteriae* Type 1, *Shigella flexneri* Type 2a, and *Shigella sonnei* (*Plesiomonas shigelloides*) Bound to Bacterial Toxoids", *Infection and Immunity*, 61, (1993), 3678-3687.

Taylor, J. L., et al., "Simultaneous Outbreak of *Salmonella enteritidis* and *Salmonella schwarzengrund* in a Nursing Home: Association of *S. enteritidis* with Bacteremia and Hospitalization", *The Journal of Infectious Diseases*, 167, (1993), 781-782.

Todar, K., "Pathogenic *E. coli*", [online]. © 2002 Kenneth Todar. [retrieved Dec. 4, 2007]. Retrieved from the Internet: <URL: http://www.textbookofbacteriology.net/e.coli.html>, 8 pgs.

Tomita, G. M, et al., "Immunization of Diary Cows with an *Escherichia coli* J5 Lipopolysaccharide Vaccine", *Journal of Diary Science*, 78, (1995), 2178-2185.

Tzianabos, A. O., et al., "The Capsular Polysaccharide of *Bacteroides fragilis* Comprises Two Ionically Linked Polysaccharides", *The Journal of Biological Chemistry*, 267(25), (1992), 18230-18235.

Wakarchuk, W., et al., "Functional Relationships of the Genetic Locus Encoding the Glycosyltransferase Enzymes Involved in Expression of the Lacto-*N*-neotetraose Terminal Lipopolysaccharide Structure in *Neisseria meningitidis*", *The Journal of Biological Chemistry*, 271(32), (Aug. 1996), 19166-19173.

Wang, Y., et al., "Structural Basis of the Abscess-Modulating Polysaccharide A2 from *Bacteroides fragilis*", *Proc. Natl. Acad. Sci. USA*, 97(25), (2000), 13478-13483.

Wright, J., et al., "Septicemia caused by *Salmonella* infection: An overlooked complication of sickle cell disease", *The Journal of Pediatrics*, 130, (1997), 394-399.

Xu, D.-Q., et al., "Molecular Cloning and Characterization of Genes for *Shigella sonnei* Form I O Polysaccharide: Proposed Biosynthetic Pathway and Stable Expression in a Live *Salmonella* Vaccine Vector", *Infection and Immunity*, 70(8), (2002), 4414-4423.

Ziegler, E., et al., "Treatment of *E. coli* and *Klebsiella* Bacteremia in Agranulocytic Animals with Antiserum to a UDP-Gal Epimerase-Deficient Mutant", *The Journal of Immunogy*, 111, (1973), 433-438.

PS Antigen ure exerted by LPS are independent of the viability of bacteria and considering the increasing resistance of pathogenic bacteria to antibiotics, the search for alternative treatment strategies for sepsis is of major importance.
ANTI-SEPSIS CONJUGATE VACCINE

CROSS-REFERENCE TO RELATED APPLICATIONS

This application is a continuation of Ser. No. 12/785,312, filed May 21, 2010, now U.S. Pat. No. 8,128,942, which is a continuation of Ser. No. 11/274,847, filed Nov. 15, 2005, now U.S. Pat. No. 7,749,511, which is a continuation-in-part of Ser. No. 10/271,253, filed Oct. 15, 2002, now U.S. Pat. No. 7,014,857, which is a continuation of PCT/US01/12417, filed on Apr. 17, 2001, which claims benefit under 35 U.S.C. 119 (e) of U.S. Provisional Application Ser. No. 60/197,739, filed Apr. 18, 2000 and U.S. Provisional Application Ser. No. 60/231,875, filed Sep. 12, 2000, which applications are incorporated herein by reference.

The invention was made with the support of the U.S. Government under Small Business Innovation Research Grant No. 1 R43A144578-01 and under Department of Defense contract no. DAMD17-03-2-0034. The Government has certain rights in the invention.

BACKGROUND OF THE INVENTION

In spite of significant improvements in antibiotic therapy and in intensive care, sepsis, and its sequelae, sepsis syndrome or septic shock (collectively, Asepsis@), remain a leading cause of morbidity and mortality among hospitalized patients. Sepsis is triggered by gram-negative and gram-positive bacteria, fungi, and other pathogenic microorganisms. These organisms release toxins at the nidus of injury or infection, that in turn trigger the release of cytokines and other mediators. If infection is not controlled, endotoxin and/or other mediators of inflammation may enter the circulation, initiating sepsis and the cascade of events that leads to endothelial damage, hypotension and multi-organ failure. Gram-negative bacteria are responsible for a large number of such episodes, which are associated with a high mortality rate. See, e.g., Centers for Disease Control, "Increase in national hospital discharge survey rates for septicemia B United States, 1979-1987," *Morbid, Mortal, Weekly Reports,* 39, 31 (1990). In patients who develop septic shock caused by gram-negative bacteria, the fatality rate may reach 50% or more. See, R. C. Bone et al., *N. Eng. J. Med.,* 317, 653 (1987). *Eseherichia coil* remains the leading causative organism, accounting for 40 to 52% of gram-negative blood isolates (S. Chamberland et al., *Clin. Infect. Dis.,* 15, 615 (1992); B. E. Kreger et al., *Am. J. Med.,* 68, 332 (1980)).

Lipopolysaccharide (LPS, endotoxin) is the major component of the outer membrane of gram-negative bacteria and is responsible for many of the pathophysiological effects observed during infections with gram-negative pathogens that may lead to septic shock and death (E. T. Rietschel et al., *Scient. Amer.,* 267, 54 (1992); *FASEB J.,* 8, 217 (1994)). Enterobacterial LPS consists of three domains, i.e., lipid A, core region and O-specific chain, of which lipid A is structurally the most conserved among different pathogenic bacteria, and represents the toxic principle of LPS (C. A. H. Raetz, *Ann. Rev. Biochem.,* 59, 129 (1990); E. T. Reitschel et al., *Infect. Dis. Clin. North Am.,* 5, 753 (1991); C. Galanos et al., *Eur. J. Biochem.,* 148, 1 (1985)). The structure of *E. coil* J5 LPS is shown in FIG. 1 (from Galanos et al. (1985)). As the toxic effects exerted by LPS are independent of the viability of bacteria and considering the increasing resistance of pathogenic bacteria to antibiotics, the search for alternative treatment strategies for sepsis is of major importance.

One of the most promising approaches for the immunotherapy of sepsis is passive immunization with antibodies that are directed against the conserved regions of LPS, i.e., lipid A and the core region. Such antibodies are expected to be cross-reactive with different gram-negative pathogens and might therefore be cross-protective. Passive immunization with polyclonal or monoclonal antibodies (Mabs) against bacterial LPS has shown protective effects in animal models of sepsis. It was shown that partially detoxified LPS from *E. coli* J5 could elicit polyclonal antibodies in rabbits that provided passive protection against *Pseudomonas aeruginosa* infections in rats (A. K. Bhattacharjee et al., *J. Infect. Dis.,* 170, 622 (1994)). Similarly, it has been shown that monoclonal antibodies against *E. coil* J5 could provide passive immune protection against heterologous bacteria challenges in mice (M. P. Schutze et al., *J. Immunol.,* 142, 2635 (1989)). See also, F. E. DiPadova et al., *Infect. Immun.,* 61, 3869 (1993); J. D. Baumgartner et al., *Immunobiology,* 187, 464 (1993). However, protection generally requires that the antibodies (Ab) be administered before sepsis pathology begins. This indicates that passive immunization has the potential to provide prophylactic protection but not therapeutic efficacy.

Prophylactic protection is best provided by active immunization, or vaccination, rather than by passive immunization. The induction of protective antibodies could potentially be achieved by immunization with LPS presented in an appropriately modified form or via mutant bacteria defective in LPS biosynthesis (rough mutants) (C. Galanos et al., *Eur. J. Biochem.,* 31, 230 (1972); S. C. Bruins et al., *Infect. Immun.,* 17, 16 (1977)). *Escherichia coli* J-5, a rough mutant of *E. coli* O111:B4, has been used in the majority of immunological studies for more than three decades in an attempt to induce broadly cross-reactive and cross-protective antibodies directed against LPS. In fact, immunization of mice with heat-killed *E. coli* J5 cells can elicit active immune protection against a challenge of the mice with *Haemophilus influenzae* type b (M. I. Marks et al., *J. Clin. Invest,* 69, 742 (1982)). See also, J. B. Baumgartner et al., *J. Infect. Dis.,* 163, 769 (1991). Multiple injections of purified, detoxified *E. coli* J5 LPS can also function as an antigen to elicit cross-protective anti-LPS Abs. A. K. Bhattacharjee et al., *J. Infect. Dis.,* 173, 1157 (1996) prepared a noncovalent vaccine using partially detoxified J5 LPS and the outer membrane protein of *N. meningitidis* Group B.

However, development of a safe and efficacious vaccine against sepsis is hindered by problems associated with the preparation of non-toxic LPS antigens that can elicit cross-protective antibodies to many kinds of bacteria. As shown in FIG. 1, the diglucosamine moiety of LPS is substituted with ester-linked phosphates, ester- and amide-linked fatty acids and with glycosidically linked polysaccharide (C. R. Raetz, *Annu. Rev. Biochem.,* 59, 129 (1990)). The non-lipid parts of the LPS molecule contain epitopes that can participate in eliciting beneficial antibodies; and the lipid (or fatty acid) substituents contain determinants of LPS toxicity (C. Galanos et al., *Eur. J. Biochem.,* 148, 1 (1985); T. Reitschel et al., *Infect. Dis. Clin. North Amer.,* 5, 753 (1991)). Thus, to detoxify LPS, attempts have been made to hydrolytically remove fatty acids while minimizing the loss of other epitopes. One approach uses mild alkaline hydrolysis that releases ester-linked fatty acids from the diglucosamine backbone. The problem with this method is that it does not release amide-linked fatty acids, and so does not provide for complete detoxification. In the case where this treatment was applied to LPS from *E. coli* J5, the partial deacylation of LPS diminished LPS pyrogenicity about 100 fold (A. K. Bhattacharjee et al., *J. Infect. Dis.,* 170, 622 (1994)). However, the partially deacylated product still exhibited pyrogenic activity at a dose lower than the dose needed to elicit protective antibodies.

The other approach for detoxification of LPS uses mild acid hydrolysis. This approach provides for greater attenuation of toxicity but causes more extensive destruction of polysaccharide epitopes. This treatment cleaves the glycosidic bond between the inner core of LPS and the lipid A diglucosamine backbone (S. J. Cryz et al. (U.S. Pat. No. 5,370,872); R. K. Gupta et al., *Infect. Immunol.*, 63, 2805 (1995); C. Galanos et al., *Eur. J. Biochem.*, 148, 1 (1985)). After hydrolysis, the polysaccharide fraction is collected for use as antigen, and the diglucosamine with attached fatty acids and phosphates is discarded. The problem with this method is that acid hydrolysis removes epitopes associated with the diglucosamine, and also partially modifies the structure of LPS polysaccharides. In the case of *E. coli* J5 LPS, mild acid hydrolysis treatment can generate polysaccharide antigens that are missing both sugar groups and phosphate groups known to be present in the polysaccharide core of native LPS. Thus, in addition to the absence of the diglucosamine backbone, the detoxified LPS polysaccharides would be depleted of ethanolamine phosphate and non-reducing terminal 3-deoxy-manno-oct-2-ulosonic acid (KDO) residues (S. Muller-Loennies et al., *Eur. J. Biochem.*, 260, 235 (1999)).

The preparation of vaccines based on detoxified LPS is also hampered by problems associated with the preparation of a suitable carrier protein for LPS antigens. A carrier protein is required because LPS polysaccharides do not have epitopes that activate helper T-cells, and without a carrier, they do not induce immune memory that is needed to elicit high titers of long-lived antibodies (J. B. Robbins et al., *J. Infect. Dis.*, 161, 821 (1990)). Detoxified bacterial toxins, such as tetanus toxin or Toxin A, referred to as "toxoids" have been used as carriers for polysaccharide antigens. When covalently linked to a carrier protein, detoxified LPS polysaccharides function as haptens and some immunogenic properties of the carrier are conferred to the linked polysaccharides. In particular, T-cell epitopes in the carrier can induce immune memory responses to the linked polysaccharide haptens.

A limitation in the use of toxoid carriers is that toxoids can cause carrier-specific epitopic suppression of haptens. In experimental animals, this phenomenon occurs when animals are immunized against a toxoid before they are vaccinated with toxoid-hapten conjugate (C. Berquist et al., *Infect. Immun.*, 65, 1579 (1997); L. A. Herzenberg et al., *Nature*, 285, 664 (1980); M. P. Schutze et al., *J. Immunol.*, 135, 2319 (1985)). There is evidence that acquired immunity to a toxoid can also cause carrier-specific epitopic suppression in humans (D. DiJohn et al., *Lancet*, 2, 1415 (1989)). Adult humans would be more likely to have immunity to toxoids than young children due to increased probability of exposure. This observation leads to a prediction that toxoid-polysaccharide conjugate vaccines would be less efficacious in adults than in young children.

Therefore, a continuing need exists for immunogenic conjugates that can provide protection against gram-negative sepsis in mammals susceptible thereto.

SUMMARY OF THE INVENTION

The present invention provides an immunogenic conjugate comprising a plurality of delipidated gram-negative bacterial lipopolysaccharide (LPS) molecules covalently linked to glucosamine residues of a molecule of *D. discoideum* Proteinase 1, which functions as the carrier molecule. The present conjugate preferably further comprises a difunctional linking molecule (or "linker") that covalently links each delipidated LPS moiety to a glucosamine residue of the Proteinase 1. The present conjugate can be used as a vaccine, to actively immunize susceptible or infected mammals, such as humans, against infection or sepsis caused by gram negative bacteria, in order to treat (prevent or to attenuate) said infection or sepsis, including its pathological consequences, including tissue or organ injury, systemic inflammatory responses and septic shock.

Anti-LPS antibodies may protect against the sequelae of sepsis caused by gram negative bacteria by at least two mechanisms—1) by binding to free LPS or bacteria-associated LPS and neutralizing the toxic effects of its lipid A moiety, or 2) by binding to LPS on the surfaces of bacteria and mediating antibody-dependent clearance and/or killing of the these bacteria. The latter mechanism may involve processes such as opsonic phagocytosis and complement-mediated lysis of bacteria. The first mechanism may primarily prevent injuries to tissues and organs in the terminal steps of sepsis wherein LPS or gram negative bacteria are released to the bloodstream. However, the second mechanism can prevent injuries that occur during the early steps of the sepsis sequelae by blocking initial infections and diseases of tissues and organs by gram negative bacteria. Accordingly, conjugate vaccines that elicits anti-LPS antibodies can protect against injuries caused by virtually any kind of gram negative bacteria that have the potential to cause infections.

Preferably, the linker is reacted with aldehyde (CHO) or acetal moieties (—OCH—OH) introduced into glucosamine residues on both the LPS and Proteinase 1 molecules. For example, amine and/or hydrazino moieties on the linker can react via a Schiff base reaction with the aldehyde or acetal moieties, followed by reduction to yield stable $CH_2$—NH linkages. Thus, methods and intermediates used to make the present conjugates are also aspects of the invention.

Deacylated LPS molecules can be prepared from gram-negative bacteria and will hereinafter be referred to as polysaccharide antigen or "PS antigen." The PS antigen can be obtained by growing the slime mold *D. discoideum* on said gram-negative bacteria under conditions such that the bacterial LPS is delipidated by cleavage of fatty acid amide and ester linkages, without loss of the lipid A diglucosamine backbone or core components such as the diphosphoryletha-nol amine (—OP(O)(OH)—O—P(O)(OH)—$OCH_2CH_2$—$NH_2$) or KDO moieties on the resultant PS antigen, thus retaining a high level of antigenicity. Preferred fermentation conditions to accomplish this bioconversion comprise growing *D. discoideum* on the gram-negative bacteria in minimal salts medium, e.g., a medium comprising about 1-10 mM magnesium ion and about 5-100 mM potassium ion in deionized water or compatible buffer. The first PS antigen isolated by this method was the delipidated LPS obtained from *E. coli* J5 LPS. The structure of this PS antigen produced by *D. discoideum* cultures is shown in FIG. 2.

This material can be treated with a phosphoromonoesterase to cleave the 1'-phosphate group to generate an acetal (or CHO) group, that can be further modified or reacted with a functional group on the linker. Therefore, both the delipidated PS antigen and the hydrolyzed PS antigen are embodiments of the present invention.

In a further embodiment, the present invention provides a biological method for detoxifying LPS from bacterial cells. In particular, a biological method is provided for isolating detoxified LPS from the J5 strain of *E. coli*. This embodied method requires that bacterial cells be prepared in a way that makes them suitable for use as a food source for cultures of *D.*

*discoideum*. It also requires that LPS in the bacterial cells contain a form of lipid A that can be deacylated by enzymes produced by *D. discoideum* cells. With these conditions met, it is reasonable to expect that the embodied methods can be used to isolate detoxified LPS antigens from several different kinds of gram-negative bacteria, including either wild type or mutant strains of medically relevant bacteria including bacteria in the families *Enterobactereaceae, Pseudomonadaceae, Neisseriaceae* and *Vibrionaceae*, as well as miscellaneous genera of gram negative bacteria causing inflammations and/or infections in human tissues and organs, such as those in the genera *Shigella, Escherichia, Salmonella, Neisseria, Pseudomonas, Vibrio, Camplyobacter, Yersinia, Haemophilus, Moraxella, Chlamydia, Franciscella, Heliobacter, Treponema, Borrelia, Leptospira, Legionella, Bacteroides, Fustobacterium, Porphyromonas, Rickettsia, Coxiella* or *Brucella*.

The novel carrier molecule for the PS antigen is a derivative of *D. discoideum* Proteinase 1. A further aspect of the invention provides a method for preparing this carrier molecule. Proteinase 1 can be isolated from the cell fraction of *D. discoideum* cultures. Molecules of PS antigen are linked to phosphorylated sugar groups in the carrier molecule, that have been modified to permit direct or indirect attachment of the PS antigens. The phosphorylated sugar moieties are believed to be the dominant B cell epitopes in Proteinase 1, and the conjugation of PS antigen essentially eliminates these epitopes while preserving the $T_h$-cell epitopes on the carrier. The replacement of carrier B-cell epitopes with PS epitopes is expected to inhibit carrier epitopes from causing epitopic suppression of immune response to the PS epitopes. This conjugation method, which is a further aspect of the invention, optimizes the ability of the carrier to amplify production of protective anti-PS antibodies in vivo that, in turn, block LPS from causing sepsis and the pathology of septic shock.

In another aspect, the present invention provides a *D. discoideum* Proteinase 1 derivative for use as a carrier molecule for moieties and antigenic haptens useful in immunogenic molecules such as conjugate vaccines. The Proteinase 1 derivative comprises a plurality of aldehyde moieties prepared by oxidative cleavage of 3,4-diol moieties of phosphorylated glucosamine moieties of *D. discoideum* Proteinase 1, or of other proteins containing analogous phosphorylated glucosamines, such as proteinases of analogous structure. Such carrier molecules can be used with the PS antigen as described in the examples hereinbelow, or can be conjugated to other detoxified bacterial LPS moieties, or to other native or synthetic haptens. For example, the present method could be used to prepare conjugate vaccines in which haptens represent protective polysaccharide or peptide epitopes for infectious disease vaccines, cancer vaccines, vaccines for atopic disease or vaccines for autoimmune diseases.

Conjugate vaccines comprising toxoids or other carrier proteins, as well as other PS antigens and haptens that can be combined with the carrier molecule and PS antigen of the invention, respectively, are disclosed, for example, in C. J. Cryz et al. (U.S. Pat. Nos. 4,771,127 and 5,370,870), Schneerson et al. (U.S. Pat. No. 5,445,819) and Parro (U.S. Pat. No. 5,306,492).

DETAILED DESCRIPTION OF THE INVENTION

The LPS Polysaccharide Antigen

Figure 1:
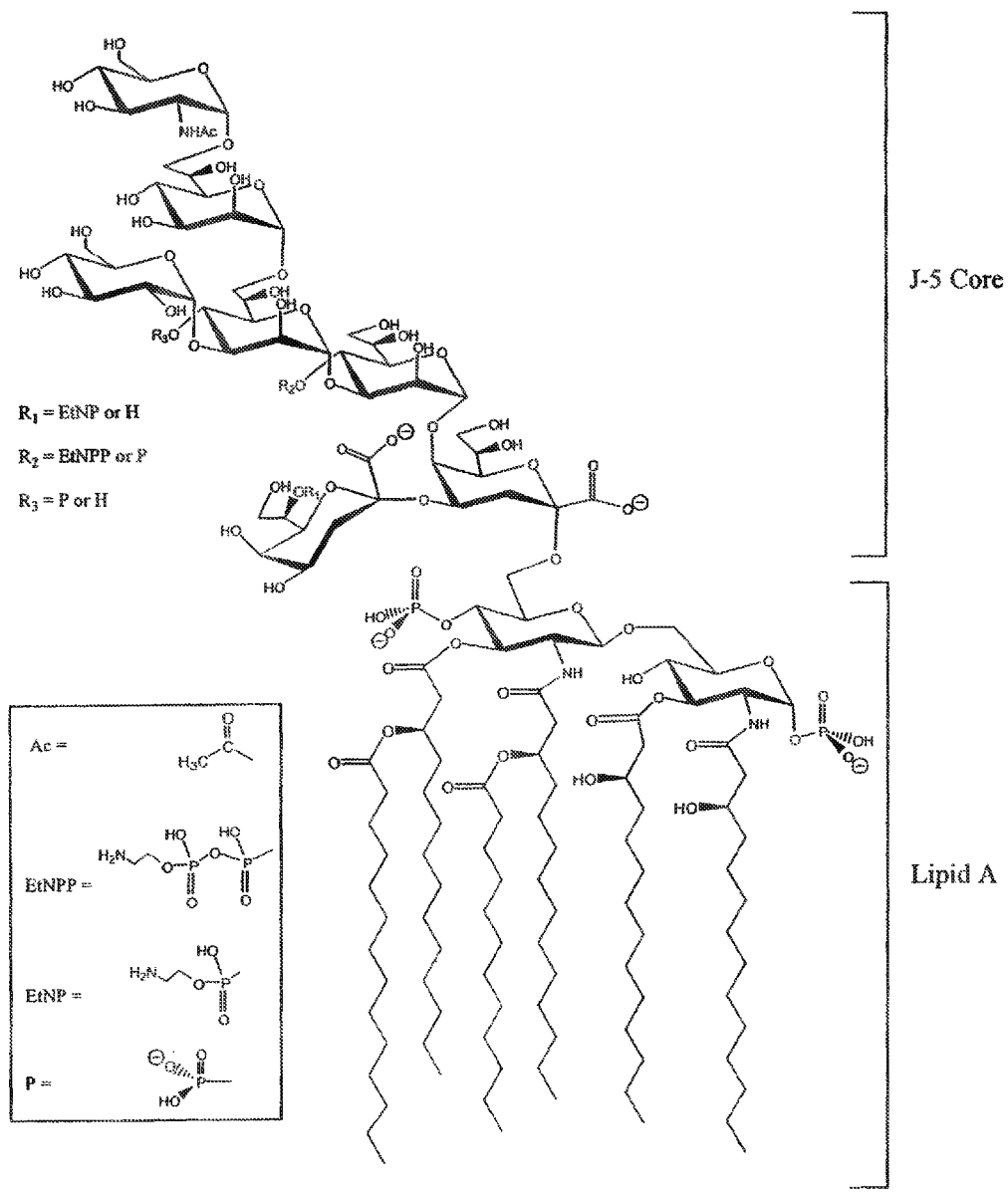
FIG. 1 depicts the structure of *E. coli* J-5 LPS.

Traditional methods of detoxifying LPS for antigen usage employ non-specific acid- or base-catalyzed hydrolytic processes to remove fatty acids from LPS polysaccharide antigens, and these processes cause undesired modifications of polysaccharide epitopes, as discussed hereinabove. In contrast, the present biological detoxification process relies on enzymes, produced by *D. discoideum* cells, to hydrolyze amide and ester bonds that link fatty acids to LPS. Because these enzymatic modifications are highly specific, this biological processing selectively removes toxic components, while preserving non-toxic epitopes needed for eliciting protective antibodies. Accordingly, the biological method of LPS detoxification, unlike chemical detoxification processes, completely deacylates LPS without hydrolyzing covalent bonds that link either diglucosamine, non-reducing terminal KDOs, or ethanolamine pyrophosphate groups to the polysaccharide of LPS.

The present method employs *E. coli* J5, and as source of PS antigen to exemplify the present method. As discussed hereinabove, native LPS from *E. coli* J5 can elicit antibodies cross-reactive with LPS from several other kinds of gram-negative bacteria. Biological processing of bacteria *E. coli* J5 by *D. discoideum* cells was employed as a means for detoxifying *E. coli* J5 LPS because previous studies indicated that *D. discoideum* cells naturally produced deacylated LPS derivatives as end-products of bacterial catabolism (D. Malchow et al., *Eur. J. Biochem.*, 2, 469 (1967); 7, 239 (1969)). These studies also suggested that *D. discoideum* cells metabolically removed ester-linked and amide-linked fatty acids from the lipid A portion of LPS, but did not hydrolyze glycosidic bonds in the polysaccharide portion of LPS. In addition, these studies indicated that antibodies elicited against native LPS recognized some LPS catabolites produced by *D. discoideum*. However, it was not known that *D. discoideum* could produce deacylated LPS from the types of bacteria useful in the present invention. Also, before the present invention, it was not known whether the forms of deacylated LPS generated by *D. discoideum*, whatever their structure, would have activity as immunogenic epitopes that would elicit antibodies that in turn, could recognize native forms of LPS. Further, prior art did not provide a method for isolating a plurality of deacylated LPS from *D. discoideum* cultures.

Thus, the present invention represents the first reported use of a cellular slime mold, such as *D. discoideum*, to biologically extract and detoxify a plurality of bacterial LPS's that are useful as vaccine antigens. The embodied biological method for producing detoxified LPS antigens is more economical and more efficacious than chemical processes used previously to prepare LPS vaccine antigens. Unlike previous isolation methods, the new biological method does not require toxic solvents to extract LPS. Further, the new process does not require LPS be chemically fractionated before it is detoxified. Instead, detoxified LPS antigens are obtained directly as water-soluble end-products that are produced by cultures of *D. discoideum* cells grown on bacteria as a food source. The antigens are readily purified from *D. discoideum* culture media by selective filtration processes and by fractional precipitation of their barium salts in ethanol-water mixtures.

A lipopolysaccharide (LPS) derivative is from a gram-negative bacterium comprising delipidated glucosamine disaccharide of lipid A and its polysaccharide. The LPS derivative of comprises at least one KDO moiety and at least one ethanolamine diphosphate group or at least one ethanolamine monophosphate group.

According to the present detoxification method, bacteria are cultured in liquid media, collected, and washed with a salt solution containing potassium chloride and magnesium chloride. When bacteria and *D. discoideum* were added to a minimal salt solution, the bacterial cells were readily phagocytosed by *D. discoideum*. The embodied methods for culturing *D. discoideum* with bacteria uses phosphate-free media containing 5 mM to 100 mM potassium ions and 1 mM to 10 mM magnesium ions. The optimal concentrations of these ions may be different when different strains of bacteria are used in the embodied methods, and a compatible buffer may also be added to the media.

Washed bacteria are suspended in the same salt solution and seeded with *D. discoideum* spores or *D. discoideum* amoebae. The resulting suspension is incubated with stirring and aeration at a constant temperature between 15° C. and 25° C. Growth and aggregation of *D. discoideum* cells is tracked by periodic, microscopic examination of culture samples.

Incubation is continued until *D. discoideum* cells cease growing and collect into multi-celled aggregates. When these conditions are met, stirring and aeration of the cultures are discontinued, and the aggregated *D. discoideum* cells are permitted to sediment from the culture media. The culture media is then separated from the sediment and filtered to remove residual cells. Next, PS antigens are isolated from the media filtrate. In one method the media is mixed with 0.2 to 0.5 volumes of ethanol and the mixture is supplemented with a water-soluble barium salt. The addition of barium ions causes the formation of barium-antigen complexes that precipitate and sediment from the ethanol-media mixture. In another method PS antigens are adsorbed to charcoal filters and subsequently eluted with solutions of alcohol, water and salt The methods of isolated PS antigens from *D. discoideum* culture media are novel. In a previous study (D. Malchow et al. cited above), LPS derivatives in *D. discoideum* culture media were concentrated by a multi-step method involving centrifugation, evaporation and dialysis processes. These methods are undesirable for purifying LPS derivatives intended for use as vaccine antigens—first, because the centrifugation and evaporation processes are costly to perform at large scale; and second, because deacylated PS antigens from some bacteria readily permeate conventional dialysis membranes.

In the present method for precipitating PS antigens from culture media, the media is adjusted to contain between 10 and 50% ethanol, and between 1 to 10 mM barium ions. A common, water soluble salt of barium, such as barium acetate or barium chloride, is used a source of barium ions. It is within the scope of these methods to substitute an alternative divalent cation for barium. For example, calcium ions may be more suitable than barium ions for precipitating some kinds of LPS antigens produced in *D. discoideum* cultures.

After incubation for at least 10 hours at a temperature of 0° C.-10° C., the sediment is collected, suspended in water, and treated with acid in order to remove barium ions from the PS antigen. Following this treatment, the PS antigen solution is neutralized by addition of an appropriate amount of a base such as potassium hydroxide, and the solubilized antigen is further purified by selective filtration and by fractional precipitation from solutions containing various concentrations of ethanol and various buffers.

Figure 2:
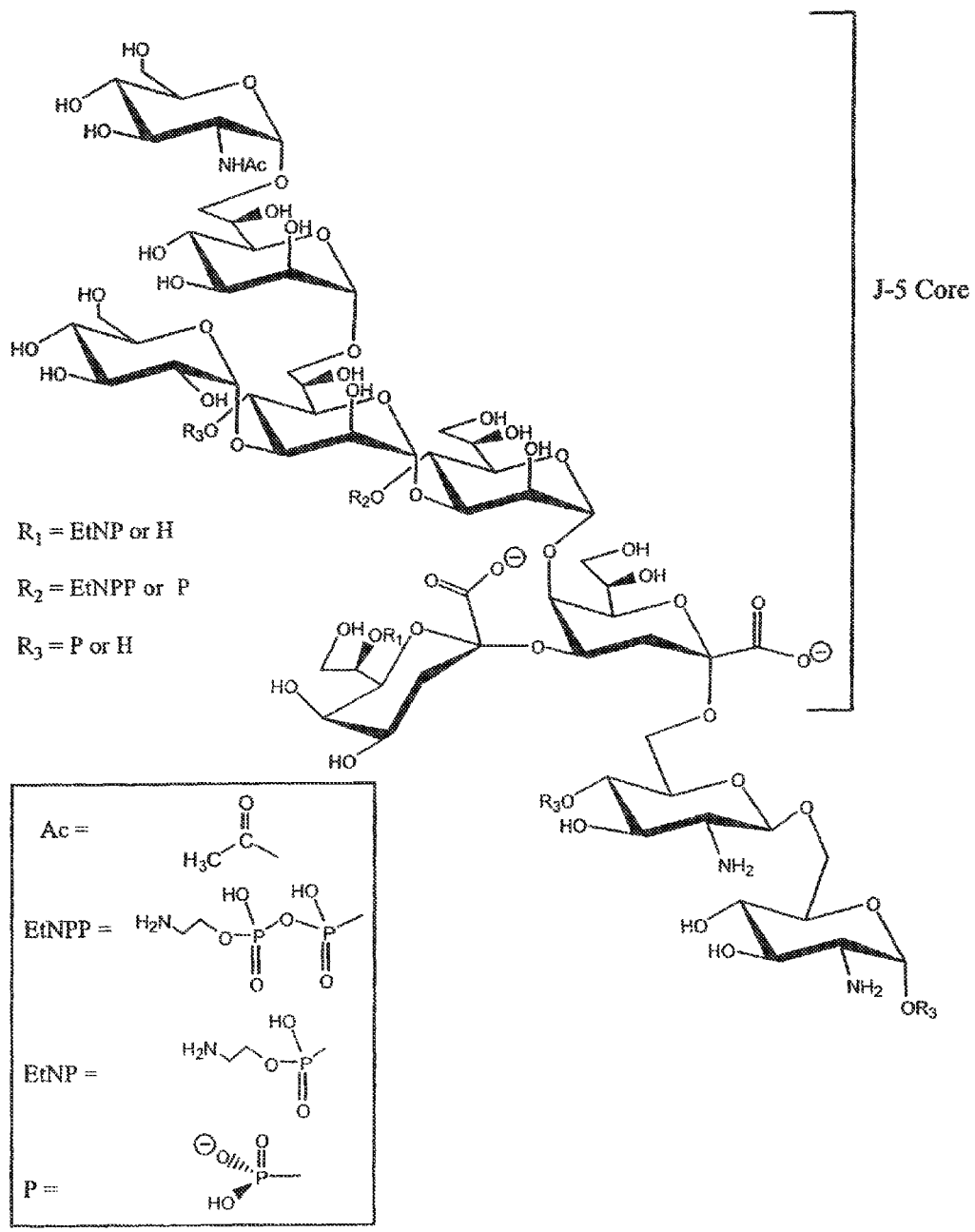
FIG. 2 depicts the structure of de-O- and -N-acetylated *E. coli* J5 LPS.

Purified PS antigen, obtained from *E. coli* J5 by the present methods, has a sugar composition similar to that determined previously for the polysaccharide portion of native LPS from *E. coli* J5 (S. Muller-Loennies et al., *Eur. J. Biochem.*, 260, 235 (1999)). The ratio of KDO:heptose:glucosamine:glucose:N-acetylglucosamine in purified antigen preparations was about 2:3:2:1:1, respectively. Phosphorous-31 NMR indicated that phosphate occurred in purified antigen molecules as diphosphodiester, and phosphomonoester forms. The structure of the *E. coli* J5 PS antigen is depicted in FIG. 2. The base structure shared by all PS antigens embodied by the present invention, comprises the diglucosamine that is present at the reducing-end of the PS antigen structure shown in FIG. 2, together with the KDO residue that is directly linked to this diglucosamine group.

Figure 3:
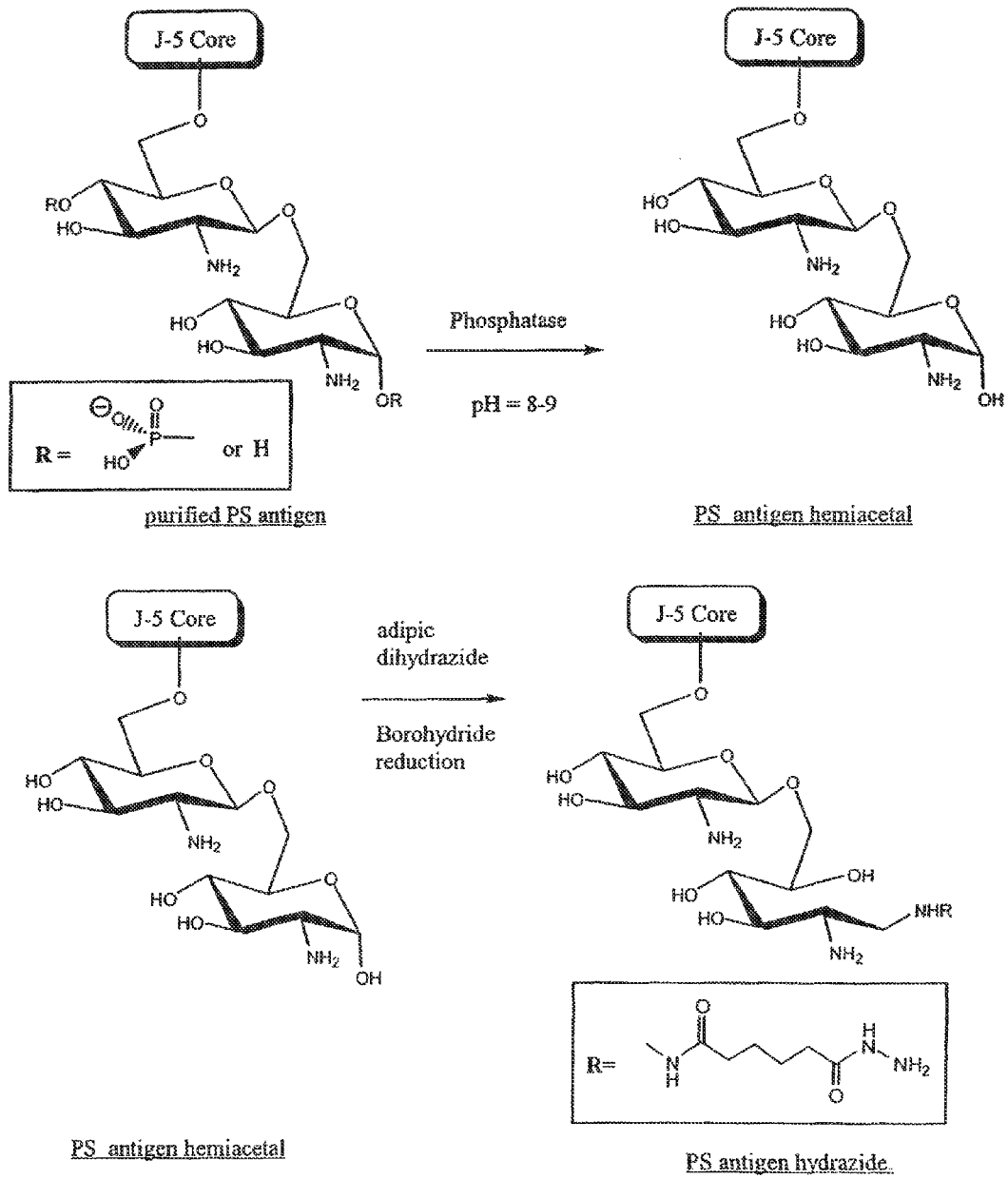
FIG. 3 depicts modification of J-5 antigen to introduce the linker group.

In a final purification step, PS antigen is treated with a phosphomonoesterase to remove the 1N-phosphate from the diglucosamine group in each antigen molecule. This treatment generates one aldehyde or acetal functional group in each antigen molecule, that can be further modified, e.g., for direct attachment to the carrier protein, or reacted with a variety of (bis)functional linking molecules. This hydrolysis reaction is depicted in FIG. 3, step (1).

Linker Molecules

Following introduction of an aldehyde or ketal into the molecule, these groups can be reacted with a bis-functional linker such as adipic dihydrazide (ADH), followed by reduction of the Schiff base, to incorporate a linker group that can be used for subsequent conjugation of PS antigen molecules to carrier protein. This reaction is depicted in FIG. 3, step 2. In this derivatization reaction, antigen is incubated at about 20-40° C. for about 20 hours in a solution of formamide containing about 10% v/v sodium acetate at pH 5, or in an aqueous buffer between pH 4-6.5, containing an excess of ADH and an excess of sodium cyanoborohydride. Sodium borohydride may be subsequently added to derivatization reactions to enhance reduction of hydrazone bonds formed between antigen and ADH. These conditions support reactions that form antigen-hydrazide molecules that contain covalent hydrazide bonds linking aldehyde groups in PS antigen to -hydrazide groups in ADH. The aldehyde group participating in this reaction represents the anomeric carbon in the reducing-end glucosamine of each PS antigen molecule.

Other linkers are available and can be used to link two aldehyde moieties, two carboxylic acid moieties, or mixtures thereof. Such linkers include ($C_1$-$C_6$) alkylene dihydrazides, ($C_1$-$C_6$)alkylene or arylene diamines, -aminoalkanoic acids, alkylene diols or oxyalkene diols or dithiols, cyclic amides and anhydrides and the like. For example, see U.S. Pat. No. 5,739,313.

Carrier Protein and Modifications Thereof

To prepare the present carrier molecule for the PS antigens, Proteinase 1, a lysosomal cysteine proteinase, was purified from *D. discoideum* cells by a novel method. Previously, Proteinase 1 was purified by methods that employed two or more chromatographic steps (G. L. Gustafson et al., *J. Biol. Chem.*, 254, 12471 (1979); D. P. Mehta et al., *J. Biol. Chem.*, 271, 10897 (1996); T. Ord et al., *Arch. Biochem. Biophys.*, 339, 64 (1997)). These earlier methods were unsuitable for use in the present method because they resulted in poor recovery of purified enzyme, and the chromatographic steps were not desirable for large-scale production of the enzyme. The novel steps in the present method of Proteinase 1 purification include steps wherein the enzyme is precipitated from aqueous ethanol in the presence of barium acetate, and a step wherein the enzyme is precipitated in the presence of high concentrations of ammonium sulfate. By substituting these novel steps for chromatographic fractionation, it is possible to manufacture purified enzyme in much higher yield and at a much greater scale than achieved previously.

To convert purified Proteinase 1 to a form suitable for use as a carrier protein, the proteinase is reacted with sodium periodate in an aqueous, buffer adjusted to a pH between pH 5 and pH 6. The preferred concentration of periodate in this reaction mixture is between 50 mM and 150 mM, and the preferred reaction temperature is between −20° C. and 20° C., preferably about 0° C., and the desired reaction is the oxidative conversion of diol groups in the N-acetylglucosamine-1-phosphate (GlcNAcP) residues to dialdehyde groups.

It is believed that other proteins containing GlcNAcP-serine moieties, such as analogous lysosomal cysteine proteinases, can be obtained from *D. discoideum* or from other slime molds, including other species of Dictyostelium or species of Polysphondylium.

The practice of the present invention can be enhanced by genetically modifying the Dictyostelium cells that are used for producing Proteinase 1. For example, genetic modifications can provide Dictyostelium mutants that (1) produce larger amounts of Proteinase 1, (2) produce an altered form of Proteinase 1 that is easier to purify, or (3) produce an altered form of Proteinase 1 that contains a larger number of GlcNAcP residues. These enhancements can be achieved by transfecting Dictyostelium cells with DNA that codes for the synthesis of natural or modified forms of Proteinase 1. Recombinant DNA techniques have been adapted for use in genetic modifications of Dictyostelium (Jenne et al., *J. Cell Sci.*, 111, 61 (1998); Moreno-Bueno et al., *Biochem. J.*, 349, 527 (2000), and Agarwal et al., *Differentiation*, 65, 73 (1999)), and the use of methods to modify the genome of Dictyostelium so as to enhance either the manufacturing of Proteinase 1 or the carrier functions of Proteinase 1 are within the scope of the present invention.

Conjugation

Figure 4:
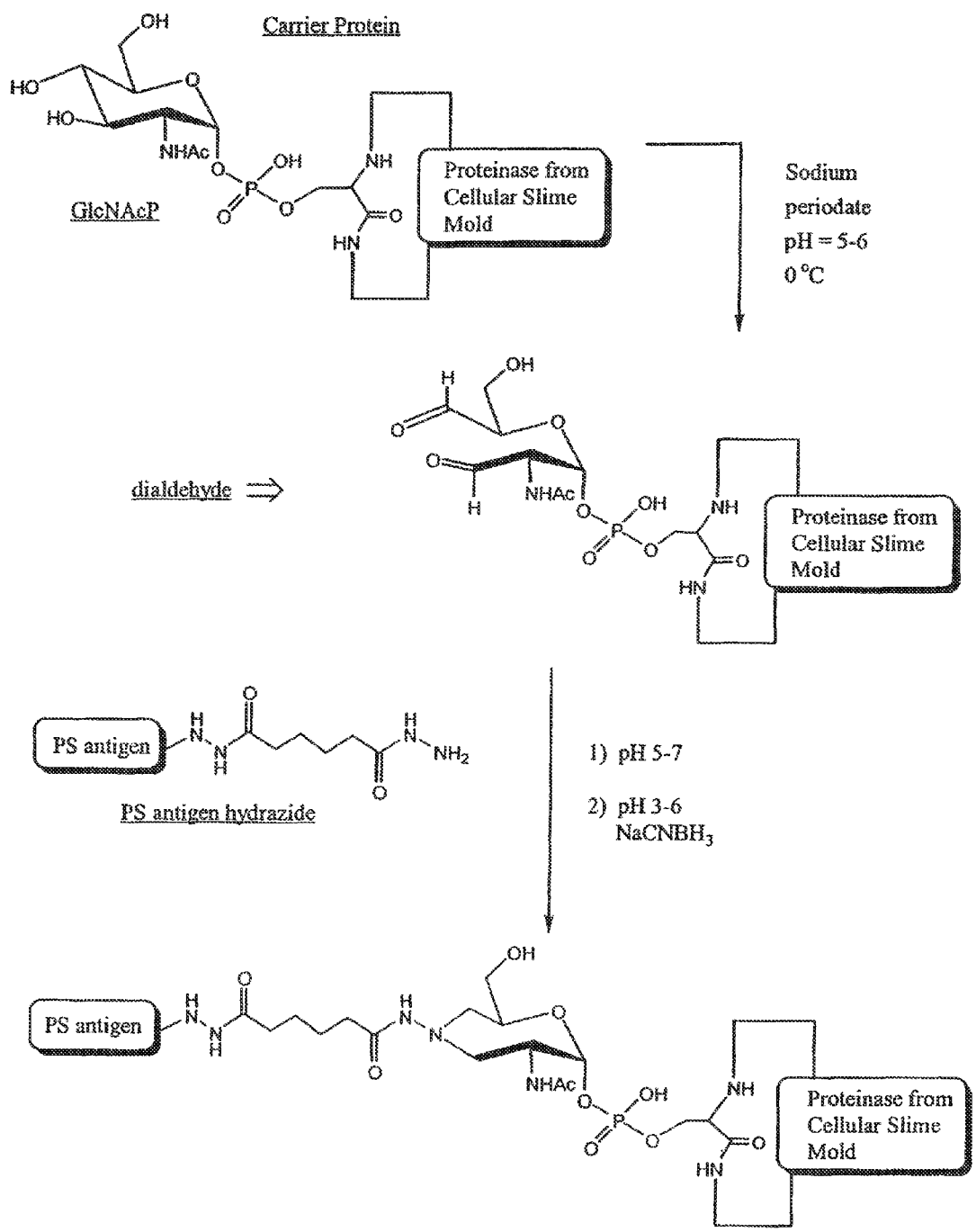
FIG. 4 depicts modification of the carrier protein to link it to the J-5 antigen hydrazide.

To conjugate the carrier protein (i.e., the oxidized proteinase) with the PS antigen-hydrazide, the oxidized protein is desalted, suspended in aqueous buffer (preferably at a pH between pH 4 and pH 7), and reacted at a temperature of about 10° C. to 30° C. for about 20-30 hrs, with antigen-hydrazide. The resulting mixture is then treated with an excess of sodium cyanoborohydride for about 24-72 hrs at about 0° C. to 20° C. As shown in FIG. 4, these conditions support reactions that generate covalent bonds between aldehyde groups in the carrier protein and hydrazide groups in PS antigen-hydrazide. With some antigens, the conjugation steps could be reversed, no that the ADH is first reacted with oxidized protease, then the free hydrazino group is reacted with an antigen aldehyde.

Upon completion of the conjugation reaction, the conjugate is separated from unconjugated antigen, desalted by dialysis, and filter sterilized. The sterile conjugate may be stored as an aqueous solution, a frozen solution, or as a freeze-dried product.

Vaccine Formulations and Vaccination

Vaccines of the invention are typically formed by incorporating the present PS antigen-carrier conjugates into pharmaceutically acceptable formulations. The formulations may contain pharmaceutically acceptable adjuvants (such as oils, surfactants, alum), immunostimulating agents (such as phospholipids, glycolipids, glycans, glycopeptides, or lipopeptides), and one or more diluents ("excipients"). Examples of diluents suitable for use are water, phosphate buffered saline, 0.15 M sodium chloride solution, dextrose, glycerol, mannitol, sorbitol, dilute ethanol, and mixtures thereof. Pharmaceutically acceptable dosage forms of the vaccines can be formulated as solutions, emulsions, dispersions, tablets, or capsules.

For human use, the vaccines are preferably administered parenterally, usually via subcutaneous or intramuscular routes of injection. Alternatively, they may be administered intraperitoneally, intravenously, or by inhalation. Oral dosage forms can also be employed, such as solutions or suspensions. In general, the vaccine of the present invention is formulated so that a dose of vaccine can be administered in a volume between 0.1 ml and 0.5 ml, but if given orally it could be administered in capsule or tablet form. The vaccine dosage, the number of doses given to an individual, and the vaccination schedule depend on the antigenicity and immunogenicity of the antigens in the conjugate and on other known pharmaceutical considerations such as the age and body weight of the individual.

The vaccines of the present invention will provide protective benefits for humans at high risk of developing sepsis and septic shock. These include elderly patients with chronic diseases, patients treated with aggressive chemotherapies or immunosuppressive therapies, patients receiving transplanted organs, and victims of severe traumatic injury. The vaccines of the present invention may also provide protective benefits in humans against one or more kinds of infections involving pathogenic gram-negative bacteria. The levels of protection obtained with the vaccine can correlate with blood titers of anti-LPS antibodies produced in vaccinated individuals. Dosages can also be extrapolated from dosages of toxoid-PS vaccines found to be safe and/or efficacious in humans. See, for example, U.S. Pat. Nos. 4,771,127 and 5,370,872.

The invention will be further described by reference to the following detailed examples, wherein colorimetric and HPLC assays were used for assessing the chemical composition of LPS-polysaccharide and PS antigen. These included assays for phosphate (B. N. Ames, *Methods in Enzymol.*, 8, 115 (1966)), glucosamine (R. L. Smith et al., *Anal. Biochem.*, 98, 478 (1979)), N-acetylglucosamine (T. A. Good et al., *Anal. Biochem.*, 9, 253 (1964)), KDO, and heptose (M. S. Osborn et al., *Biochemistry*, 50, 499 (1963)), glucose, Sigma Chemicals, St. Louis, Mo., Kit #510-A, (E. Raabo et al., *Scand. J. Clin, Lab. Invest.*, 12, 402 (1960)), and aldehyde functional groups (J. T. Park et al., *J. Biol. Chem.*, 181, 149 (1949)). Recovery of polysaccharide through various purification steps was monitored by the phenol-sulfuric acid assay (G. Ashwell et al., *Arch. Biochem. Biophys.*, 42, 648 (1965)). Ethanolamine, ethandamine phosphate and diglucosamine were monitored by HPLC. Enzymatic activity of Proteinase 1 was determined as previously described by G. L. Gustafson, cited above. All centrifugation processes were performed at 3600×g for 15 min at 5° C. Nuclear magnetic resonance spectroscopy was performed using a Varian Unity 400 MHz NMR instrument. Trichloroacetate Buffer (TCAB), for fractionation of Proteinase 1 was either purchased as the sodium salt or was prepared by titrating a 4 M solution of cold trichloroacetic acid with cold 4 M sodium hydroxide to a final pH of 1.5. All Tricine buffers were prepared at pH 8.

EXAMPLE 1

Production of *D. discoideum* Cells and Crude Deacylated LPS from Gram-Negative Bacteria A. Materials Yeast extract, tryptone, dextrose, and agar were from Difco Laboratories, Detroit, Mich. All other chemicals were reagent grade.

B. Organisms and Growth Conditions

1. Cell Lines. *D. discoideum*, strain NC-4 (ATCC 24697), and *E. coli*, strain J5 (ATCC 43475), were obtained from the American Type Culture Collection, 1081 University Boulevard, Manassas, Va. Stocks of *D. discoideum* NC-4 spores and *E. coli* J5 cells were stored in 33% and 15% glycerol, respectively, at −80° C. Pa3 is a rough LPS mutant derived from *Pseudomonas aeruginosa* (ATCC 33354).

2. Recipes. Nutrient Broth (NB): 10 g Tryptone, 10 g dextrose, 1 g yeast extract, 0.247 g (1 mM) magnesium sulfate heptahydrate, 0.378 g (2.7 mM) dibasic sodium phosphate, 1.44 g (10.6 mM) monobasic potassium phosphate brought to one liter in deionized water. Nutrient Agar (NA): 1 L of NB plus 15 g agar. Nutrient Media 1 (NM1): 18 mM potassium phosphate buffer, pH 6.9, 20 g Tryptone, 30 g dextrose, 3 g yeast extract, 0.0255 g (0.23 mM) $CaCl_2$, 0.5 g (3.8 mM) ammonium sulfate, 0.45 g (2 mM) magnesium sulfate, 0.0427 g (0.18 mM) sodium citrate, 0.012 g (0.08 mM) ferrous sulfate, and 1.0 ml trace elements brought to one liter in deionized water. Nutrient Media 2 (NM2): NM1 without yeast extract. Magnesium Media-1 (MgM-1): 5 mM magnesium chloride and 15 mM potassium chloride in deionized water.

3. Working Cultures. Microorganisms were freshly prepared for each production run. For a working culture of *E. coli* J5, stock cells were streaked on sterile nutrient agar plates and incubated at 37° C. for three days. For a working culture of Pa3, stock cells were streaked on sterile TSA plates and incubated at 37EC for 24-48 hrs. For a working culture of *D. discoideum* spores, stock cells of *E. coli* J5 and stock spores of *D. discoideum* were spread on sterile nutrient agar plates and incubated for one week at 20° C.

4. Seed Cultures. Seed bacteria were prepared by inoculating 3 liters of sterile NM1 with a working culture of *E. coli* J5, or Pa3, and incubating 10-16 hours at 37° C. Bacteria in the resulting cultures were collected by centrifugation and washed with sterile MgM-1. Seed. cultures of *D. discoideum* amoebae were prepared by inoculating 1 liter of MgM-1 with 12 gm (wet weight) seed bacteria, $2 \times 10^8$ *D. discoideum* spores, and the culture incubated 30 to 40 hours at 20° C.

5. *E. coli* J5 and Pa3 Feed Bacteria: Feed bacteria were prepared by inoculating 15 L of NM2 with 6 g of the washed *E. coli* J5 or Pa3 seed bacteria, and incubating the culture at 37° C. with stirring, aeration, and pH control until the culture entered stationary phase. The feed bacteria were collected by centrifugation and washed with sterile MgM-1. Typically, the wet weight yield of washed bacteria was between 400 to 500 g for *E. coli* J5, and between 200-400 g for Pa3. These bacteria were used to feed the 15 L *D. discoideum* cultures.

6. Culture Conditions. Fifteen liters of sterile MgM-1 was supplemented with 120-160 gm (wet weight) of washed feed bacteria, inoculated with 1 liter of *D. discoideum* seed amoebae, and incubated at 20° C. with stirring and aeration. When essentially all of the bacteria had been consumed, *D. discoideum* cells were separated from the culture media, washed with 25 mM potassium chloride, and stored frozen at −80° C. for later use in preparing Proteinase 1. The culture medium, containing crude deacylated LPS, was collected separately for use in preparing polysaccharide antigen.

7. Isolation of PS Antigen. Fifteen to seventeen liters of centrifuged culture media, containing crude deacylated LPS, were passed through a ZetaPlus® 60SP pharmaceutical grade depth finder. The filtrate was supplemented with 0.5 M Tricine buffer (20 ml/L of filtrate), 1 M barium acetate or barium chloride (4 ml/L of filtrate), 95% ethanol (300 ml/L of filtrate), and incubated at 4° C. for 10-20 hours. The incubation mixture from Step 2 was centrifuged; the pellet suspended in 400 ml deionized water, and brought to pH 3 by addition of sulfuric acid. The pH of the acidified suspension was re-adjusted to pH 8 by addition of potassium hydroxide. This suspension was centrifuged, and the barium sulfate pellet discarded.

The supernatant was brought to 10 mM EDTA, mixed with an equal volume of 95% ethanol, and the resulting mixture incubated at −20° C. for 30 minutes. Precipitated polysaccharide antigen was collected by centrifugation. The pellet was dissolved in 150 ml of 50 mM sodium acetate buffer (pH 4.5), mixed with an equal volume of 95% ethanol and allowed to incubate at −20° C. for 30 minutes. The precipitated polysaccharide antigen was again collected by centrifugation.

The pellet was dissolved in 30 ml of 50 mM sodium acetate buffer (pH 4.5) and passed through a 5,000 molecular weight cut-off filter in a stirred cell under 30 psi pressure. The filter was then washed by passing through an additional 30-50 ml of sodium acetate buffer (pH 4.5). This wash was added to the first filtrate, mixed with 2 volumes of 95% ethanol, and incubated at −20° C. for 10-20 hours. Precipitated polysaccharide antigen was collected by centrifugation. The pellet was dissolved in 10-15 ml of deionized water, brought to 150 mM Tricine pH 8.0, mixed with 2 volumes of 95% ethanol and incubated at −20° C. for 1-20 hours. Precipitated polysaccharide antigen was collected by centrifugation.

The purified antigen was re-dissolved in deionized water at approximately 10 to 20 mg/ml and digested for 1-2 h at 56° C. with alkaline phosphatase to remove residual phosphate from the reducing end of diglucosamine backbone. Completion of phosphate release was verified by monitoring the aldehyde to KDO ratio using the standard colorimetric assays. Phosphatase-treated PS antigen was separated from alkaline phosphatase by filtration through a 5,000 molecular weight cut-off filter. The initial filtrate and subsequent wash were pooled as before and brought to 150 mM Tricine, pH 8.0. Two volumes of 95% ethanol were added to the pooled filtrates and the mixture incubated at −20° C. for 2-24 hours. Precipitated phosphatase-treated PS antigen was collected by centrifugation. The purified, hydrolyzed PS antigen was resuspended in deionized water, distributed to the desired number of serum vials, shell frozen, lyophilized, capped, and stored until used to make PS antigen hydrazide.

EXAMPLE 1B

Production of PS Antigens from *Shigella flexneri* 2a and *Neisseria meningitidis*

A. Organisms and Growth Conditions.

1. Cell Lines. *Shigella flexneri* 2a, substrain BS103 and an acapsular mutant (SynX knockout mutant) of *Neisseria meningitidis*, strain 9162 were obtained from the Walter Reed Army Institute of Research, Silver Springs, Md. *D. discoideum* was the same strain as used in Example 1. Master and working cell banks of both the bacteria and of *D. discoideum* spores were stored frozen at −80° C.

2. Fermentation of *S. flexneri* 2a and *N. meningitidis*. *S. flexneri* 2a was cultured in a conventional type fermenter operated at 37° C. with stirring, aeration, and pH control. The growth media contained 30 g/L yeast extract, 20 g/L glycerol, and 10 g/L NaCl. Bacteria were harvested at early stationary phase and washed with sterile MgM-1. The resulting cell paste was stored frozen at −80° C. until used for fermentation of *D. discoideum*.

*N. meningitidis* was cultured in a fermenter fitted with marine impellers. The stirring speed was 250 RPM. Dissolved oxygen was maintained at about 60% of air saturation, the pH setpoint was 7.0, and the temperature setpoint was 37° C. The growth media was composed of equal amounts of the following five solutions: Solution 1. $NH_4Cl$ (2.0 g/L), KCl (0.84 g/L), NaCl (29.25 g/L) $Na_2HPO_4$ (5.325 g/L), KH2PO4 (0.85 g/L), and sodium citrate (3.235 g/L); Solution 2. $CaCl_2.2H_2O$ (0.185 g/L) and glucose (50 g/L); Solution 3. yeast extract (50 g/L); Solution 4. ferric citrate (0.2 g/L); and Solution 5. $MgSO_4.7H_2O$ (3.08 g/L) and $MnSO_4.H_2O$ (0.025 g/L). The five solutions were autoclaved separately and aseptically combined after cooling.

As with S. flexneri 2a, N. meningitidis was harvested from the fermenter when the culture reached the early stationary phase of growth. Bacteria were washed with MgM-1, and stored as a frozen cell paste at −80° C.

4. Culture Conditions for D. discoideum. Magnesium Media-2 (MgM-2) was substituted for MgM-1 for culturing D. discoideum on S. flexneri 2a and N. meningitidis. MgM-2 contained 5 mM magnesium chloride, 67 mM 1,4-piperazinediethanesulfonic acid, and sufficient potassium hydroxide to adjust the pH value of the media to about 6.5. The concentration of potassium ions in MgM-2 was approximately 60 mM.

For fermentation of D. discoideum on either S. flexneri 2a or N. meningitidis, bacteria paste was suspended in sterile MgM-2 to a density of about 40 g wet wt./liter, and the media was then inoculated with D. discoideum amoebae to a density of about $1-2\times10^6$ amoebae/liter. The resulting suspension was incubated in a conventional fermenter operated at about 20° C. with continuous stirring and aeration. When the majority of bacteria had been consumed, the culture was centrifuged to separate the culture media from D. discoideum cells and residual bacteria. The supernatant fluid, containing the cell-depleted culture media, was collected for use in the preparation of PS antigens, and the sedimented fraction, containing D. discoideum and bacteria cells, was discarded. The pH of the culture media fraction was next adjusted to a value of about 2.3-2.5 by addition of an appropriate volume of 5N HCl. This acidification of culture media provided for the precipitation of piperazinediethanesulfonic acid. After a second centrifugation to remove this precipitate, the pH the media was readjusted to a value of about pH 6 by addition of an appropriate volume of 0.5 N NaOH. The resulting media fraction was stored frozen at −20° C. until used for isolation of PS antigen.

5. Isolation of PS Antigens. To purify and concentrate PS antigens, buffer-depleted media obtained from D. discoideum cultures was sequentially passed through 1) type R31 coal-based activated carbon filters (Cuno, Inc.) and 2) type R33 peat-based activated carbon filters (Cuno, Inc.). The first type of filter decolorized the media, and the second type of filter adsorbed the majority of PS antigens. The adsorbed PS antigens were subsequently recovered from type R33 carbon filters by elution with solutions containing mixtures of water, ethanol, and NaCl.

Two fractions of Shigella PS antigens were obtained from D. discoideum cultures that were fed S. flexneri 2a—one fraction (designated as sPS) contained PS antigens with small O-specific polysaccharides, and the other fraction (designated as 1gPS) contained PS antigens that had large O-specific polysaccharides. The sPS fraction was eluted from type R33 carbon filters with a solution containing about 20% ethanol and about 0.05 M NaCl, and the 1gPS fraction was eluted from type R33 carbon filters with a solution containing about 50% ethanol and 0.25 M NaCl. PS antigen derived from N. meningitidis eluted from type R33 carbon filters under conditions similar to those used for elution of the sPS fraction from Shigella. The amounts of PS antigens obtained from a D. discoideum culture that was fed S. flexneri 2a were approximately 40 μmoles sPS/liter of culture media and 3 μmoles 1gPS/liter of culture media; and the amount of PS antigen obtained from a D. discoideum culture that was fed N. meningitidis was approximately 25 μmoles PS/liter of culture media.

PS antigens derived from S. flexneri 2a and N. meningitidis were further purified by ultrafiltration. The resulting PS antigen fractions were adjusted to pH 8.5 and treated with alkaline phosphatase at 37° C. to remove phosphate from the reducing end of the diglucosamine backbone of PS antigens. Following this treatment, the PS antigens were desalted by dialysis and lyophilized.

EXAMPLE 2

A. Preparation of Antigen Hydrazide (Method I)

Method I has been used to prepare antigen hydrazide for PS antigen derived from E. coli J5.

Adipic dihydrazide (2.48 g) was dissolved in 63.9 ml of formamide to give solution 1. Purified phosphatase-treated PS antigen (280 mg) ("PS antigen aldehyde") was dissolved in 7.1 ml of 2 M sodium acetate buffer (pH 5) to give solution 2. Solutions 1 and 2 were combined and supplemented with 1.34 g sodium cyanoborohydride to give solution 3.

Solution 3 was brought to pH 7.5 by addition of glacial acetic acid and incubated at room temperature for 20 hours. During the first 12 hours of this incubation period, the pH of the solution was maintained near pH 7.5 by periodic additions of glacial acetic acid.

After incubation, the solution was supplemented with 71 ml of 0.5 M Tricine buffer, 0.5 ml of 1 M barium acetate, and 140 ml of 95% ethanol; and the mixture incubated at −20° C. for 1 h. The incubated mixture was centrifuged, the pellet collected, dissolved in 22 ml of 0.5 M Tricine buffer containing 25 mg sodium borohydride, and incubated at room temperature. Three additional 25 mg portions of sodium borohydride were added to the mixture at 15 min intervals over the course of a 1 h incubation period.

PS antigen hydrazide was precipitated from the reaction mixture by adding 22 ml of deionized water, 88 ml of 95% ethanol, and 0.2 ml of barium acetate to the reaction mixture. The precipitated PS antigen hydrazide was collected by centrifugation, the pellet was dissolved in 44 ml of 0.25 M Tricine containing 1.5 mM barium acetate, and re-precipitated by addition of 88 ml of 95% ethanol. The reprecipitation step was repeated, and the resulting washed PS antigen hydrazide was filtered through an 8000 molecular weight cut-off membrane.

The filtered PS antigen hydrazide was precipitated with two volumes of 95% ethanol, collected by centrifugation, and the pellet was dried in vacuo.

B. Preparation of Antigen Hydrazide (Method II)

Method II has been used for preparing antigen hydrazide for PS antigens from E. coli J5 and P. aeriginosa Pa3.

Adipic dihydrazide (2.63 g) and sodium cyanoborohydride (1.43 g) were added to a solution of phosphatase-treated polysaccharide antigen (300 mg) in 0.5M MES buffer pH 6.3 (75 mL). The reaction was stirred and incubated at 37° C. for 20 hours.

After this incubation, the reaction mixture was supplemented with dry CHES buffer (7.77 g) and the solution was then adjusted to pH 9.0 with sodium hydroxide. Two additions of sodium borohydride (700 mg) were made to the reaction at 30 minute intervals while incubating at ambient temperature for 1 hour. The antigen hydrazide was recovered by centrifugation (3600 rpm for 15 minutes at 4° C.) after precipitation with 95% ethanol (200 mL) and incubation at −20° C. for 1 hour.

The pellet was dissolved in water (70 mL) and 0.5M Tricine pH 8.0 (30 mL) and precipitated by adding 95% ethanol (200 mL) and incubating at −20° C. for 1 hour. The antigen hydrazide was recovered by centrifugation as above.

The antigen hydrazide pellet was dissolved in water (70 mL) and 0.9% saline (30 mL) then precipitated and recovered by centrifugation as above. The pellet was dissolved in water (50 mL), frozen at −80° C. and lyophilized to dryness.

C. Preparation of Antigen Hydrazide (Method III)

Method III has been used for preparing antigen hydrazides for PS antigens from *S. flexneri* 2a and *N. meningitidis*. Reaction mixtures were prepared in water and contained the following concentrations of reactants: PS antigen (0.4 to 4 mM), MES buffer at pH 6-6.5 (400 to 1500 mM), adipic dihydrazide (200 to 600 mM), sodium cyanobrohydride (400 to 800 mM). Reaction mixtures were incubated for about 20-30 hours at 37° C., and then desalted by dialysis.

D. Preparation of Antigen Hydrazide (Method IV)

Reaction mixtures used for Methods I-III contained significant amounts of borate ion. This borate was generated from the decomposition of sodium borohydride that occurred as a contaminant in the cyanoborohydride reagent. When borate deficient reaction mixtures comparable to those used in Method III were prepared, using a refined grade of cyanoborohydride (lacking sodium borohydride), it was found that supplementation of the reaction mixtures with borate ion markedly stimulated formation of antigen hydrazide. Accordingly, borate may play an important role in facilitating antigen hydrazide production. A reaction mixture that provided satisfactory production of the antigen hydrazide derivative of *E. coli* J5 PS antigen contained the following concentrations of reagents: 1.8 mM PS antigen, 400 mM MES buffer at pH 6.1, 180 mM adipic dihydrazide, 120 mM sodium cyanoborohydride, and 160 mM boric acid.

EXAMPLE 3

Isolation of Proteinase 1

A frozen cake of *D. discoideum* cells (500 to 600 gm wet wt.) was suspended in 3 mM dithiothreitol (2.25 ml/gm cells), and the suspension was equilibrated at a temperature of about 4° C. Cold, TCAB (0.75 ml/gm cells) was added to the suspension with stirring, and the resulting mixture was then titrated with cold 0.5 N HCl to a final pH of approximately 2.4. The titrated mixture was centrifuged and the supernatant fluid was collected for further fractionation of Proteinase 1. Cold 0.5 M Tricine buffer (0.5 ml/gm cells) was added to the supernatant fluid, and the mixture was adjusted to pH 8 by addition sodium hydroxide. This solution was designated as fraction F1.

Fraction F1 was mixed with 95% ethanol (0.67× volume F1), and the mixture was incubated 1.5 h at −20° C. After centrifugation, supernatant fluid was collected and supplemented with 95% ethanol (1/3× volume F1), and with 1 M barium acetate (0.004× volume F1). After incubation at −20° C. for 1.5 h, the mixture was centrifuged, the pellet collected, and suspended in 600 ml of buffer containing 10 mM Tricine/4 mM dithiothreitol (10T/4D). This suspension was centrifuged, and the supernatant fluid (fraction F2) was collected.

Fraction F2 was mixed with 95% ethanol (1× volume F2) and 1 M barium acetate (1/500× volume F2). After incubation at −20° C. for 1 h, the mixture was centrifuged, the supernatant was discarded, and the pellet was suspended in 150 ml 10T/4D buffer. This suspension was centrifuged and the supernatant fluid (fraction F3) was collected.

Fraction F3 was mixed with 95% ethanol (1× volume F3) and 1 M barium acetate (0.002× volume F3). After incubation at −20° C. for 1 hour, the mixture was centrifuged, the supernatant was discarded, and the pellet was suspended in 80 ml 10T/4D buffer. The suspension was centrifuged, and the supernatant fluid (fraction F4) was collected.

Fraction F4 was mixed with 95% ethanol (1× volume F4) and 1 M barium acetate (0.002× volume F4). After incubation at −20° C. for 1 h, the mixture was centrifuged, the supernatant was discarded, and the pellet was suspended in 40 ml 10T/4D buffer. The suspension was centrifuged, and the supernatant fluid (fraction F5) was collected.

Fraction F5 was mixed with 95% ethanol (0.15× volume F5). After incubation at −20° C. for 1 h, the mixture was centrifuged, the pellet was discarded, and the supernatant was mixed with ethanol (0.85× volume F5). After incubation at −20° C. for 1 hour, the mixture was centrifued, the supernatant was discarded, and the pellet was suspended in 10 ml 10T/4D buffer (fraction F6).

Fraction F6 was dialyzed against 10T/4D buffer, and the dialysate was mixed with an equal volume of 4 M ammonium sulfate. After centrifugation, the supernatant fluid was collected (fraction F7).

Proteinase 1 was precipitated from F7 by treatments with additional ammonium sulfate. The precipitate was collected by centrifugation and dissolved in a small volume of 5 mM ammonium bicarbonate, dialyzed against additional 5 mM ammonium bicarbonate, and lyophilized to yield purified Proteinase 1.

EXAMPLE 4

Synthesis of Proteinase 1-PS Antigen Conjugate (Method 1)

Purified Proteinase 1 was oxidized to introduce dialdehyde side chain moieties as follows: 1) about 35 mg of the proteinase was dissolved in 25.5 ml 0.1 M sodium acetate (pH 5) containing 545 mg sodium periodate, and the resulting mixture was incubated in an ice bath in the dark at 4° C. for 20 hours, 2) the mixture was then supplemented with 5 ml 50% glycerol and incubation in an ice bath was continued for an additional 2 hours. The product of this reaction was dialyzed and concentrated in a stirred, dialysis chamber, equipped with dialysis membrane having a 10,000 molecular weight cut-off. The resulting solution was adjusted to contain 0.1 M sodium acetate (pH 5) in a final volume of about 10 ml.

Dry PS antigen hydrazide (about 280 mg) was dissolved in this solution of oxidized Proteinase 1 to form a conjugation reaction mixture. The reaction mixture was incubated at room temperature for about 16 hours. It was then supplemented with 3 ml of 0.5 M sodium acetate (pH 5) and 169 mg sodium cyanoborohydride and incubation was continued at room temperature for an additional 20 hours to yield Proteinase 1 linked to a plurality of PS antigen moieties by HNHNC(O) $(CH_2)_4C(O)NHN$ linkers.

Carrier-antigen conjugate was then separated from unconjugated antigen hydrazide by filtration of the reaction mixture in a stirred dialysis chamber equipped with a membrane having a 5000 molecular weight cut-off. The conjugate product was retained on the membrane and collected in 15 ml of 10 mM Tricine buffer.

Residual barium ions in the buffer solution were precipitated as barium sulfate after addition of 0.02 ml of 4 M ammonium sulfate. The precipitate was removed by centrifugation, and the resulting supernatant fluid was dialyzed against 5 mM ammonium bicarbonate and lyophilized. The lyophilized, conjugate vaccine contained about 18 mg of carrier protein and about 26 mg of polysaccharide antigen.

Synthesis of Proteinase 1-PS Antigen Conjugate
(Method 2)

Purified Proteinase 1 was dissolved in acetate or succinate buffer (pH 5-6) at a concentration of approximately 10 mg/ml. The resulting solution was mixed with an equal volume of 0.2 M periodate, and the resulting reaction mixture was incubated in an ice bath in the dark for about 20-30 hours. The oxidation reaction was terminated by quenching the remaining periodate with excess of sodium sulfite. Following this treatment, the resulting oxidized Proteinase 1 was supplemented with PS antigen hydrazide, sodium cyanoborohydride, and succinate buffer to give a solution containing 5 mg/ml oxidized Proteinase, 0.750-1.250 μmole/ml PS antigen hydrazide, 30 μmol/ml sodium cyanoborohydride, and 200 μmol/ml succinate, pH 5.5. Additional sodium cyanoborohydride was added at 24 h and 48 h of incubation.

The conjugate product was separated from unconjugated PS antigen hydrazide and other components of the reaction mixture either by ultrafiltration or gel exclusion chromatography.

EXAMPLE 5

Ability of Proteinase 1-Based Carrier to Potentiate Immunogenic and Immune Memory Responses to *E. coli* J5 PS-Antigens To prepare a vaccine with antigen-carrier conjugate, a sample of conjugate was dissolved in an appropriate volume of 0.1% polysorbate 80 to give a solution containing 10 vaccine doses per 0.1 ml solution. An equal volume of Freund's incomplete adjuvant was added to this solution, and the mixture was emulsified. The resulting emulsion was diluted with four volumes of 0.1% polysorbate 80 to give a final emulsion containing 10 vaccine doses/1 ml. Separate emulsions were prepared for each dose level of antigen-carrier conjugate, and each dose was delivered in a total volume of 0.1 ml.

Each vaccine dose was administered to a separate group of mice by subcutaneous injections. Groups were assembled randomly from age-matched populations of mature, female ICR mice. Blood samples from immunized mice were collected in heparin and equal aliquots of individual plasmas from each group of mice were pooled for antibody analyses. Antibody titers were determined by ELISA using normal immune serum (pooled from 10 unvaccinated mice) as a negative control and monoclonal antibody against *E. coli* J5 LPS as a positive control.

Preliminary studies (data not shown) indicated that primary and secondary immunizations of mice with unconjugated PS antigen elicited only trace amounts of antibodies reactive in ELISA with LPS from either *E. coli* J5 or *Salmonella enteritidis* (SE). These results agreed with other studies showing that unconjugated LPS polysaccharides are weak antigens.

Table 1, below, summarizes the ELISA results from mice given primary, secondary and tertiary doses of conjugate vaccine containing *E. coli* J5 PS antigen and carrier protein. A primary vaccine dose was given at age 15 weeks. A secondary booster vaccine dose was given 24 days after the primary dose, and a tertiary booster dose was given 11 days after the secondary dose. Group 1 mice received 25 μg doses of antigen-carrier conjugate in each injection, Group 2 mice received 50 μg doses of conjugate, and Group 3 mice received 100 μg doses of conjugate.

TABLE 1

| Schedule | Dose in μg | Anti-J5 Titer* | Anti-SE Titer* |
| --- | --- | --- | --- |
| Primary | 25.0 | 710 | 1080 |
|  | 50.8 | 670 | 1720 |
|  | 100.0 | 830 | 1590 |
| Secondary | 25.0 | 15600 | 42370 |
|  | 50.8 | 13700 | 34800 |
|  | 100.0 | 20000 | 53400 |
| Tertiary | 25.0 | 23800 | 60300 |
|  | 50.8 | 22700 | 83600 |
|  | 100.0 | 19600 | 56100 |

*Titers were determined at an $OD_{450}$ reading of 0.1 plus background. The average $OD_{450}$ background was approximately 0.065.

The results show that primary immunizations of mice with conjugate vaccine elicited anti-LPS antibody titers between 700-1700; and that secondary immunizations boosted antibody titers about 20 to 30 fold. These results demonstrate that the carrier protein enhanced both the immunogenicity and T-cell dependence of polysaccharide antigens conjugated to it. The amplification of antibody titers observed between respective primary and secondary and between respective secondary and tertiary vaccine doses demonstrates that the carrier protein elicits immunological memory of linked PS antigens. No significant difference ($P>0.05$) was observed between the tertiary antibody titer elicited by the 100 μg vaccine dose and tertiary antibody titers elicited by either the 25 μg or 50 μg doses of PS antigen-carrier conjugate.

EXAMPLE 6

Ability of *E. coil* J5 PS Antigen Conjugate Vaccine to Elicit Cross-Reactive Anti-LPS Antibodies Table 2 presents data on the cross-reactivity of antibodies elicited by conjugate vaccines containing PS antigen from *E. coli* J5. The mice in all experiments were mature, out-bred, female ICR mice. Four different lots of conjugate vaccine were used. Mice in E1 received 200 μg of Lot-1 vaccine for the primary injection, 200 μg of Lot-3 vaccine for the secondary injection 7 weeks later, and 200 μg of Lot-4 vaccine for the tertiary injection 11 weeks after the primary injection.

Mice in E2 received 200 μg of Lot-2 vaccine for the primary injection, 200 μg of conjugate Lot-3 vaccine for the secondary injection 6 weeks later, and 200 μg of conjugate Lot-4 vaccine for the tertiary injection 10 weeks after the primary injection.

Mice in E3 received 25 μg of Lot-4 vaccine for the primary injection and 25 μg of Lot-4 vaccine for the secondary injection 3 weeks later.

Plasma was collected 2 weeks after tertiary vaccinations, for E1 and E2, and 11 days after the secondary vaccination for E3. Equal aliquots of plasma from mice in each group were pooled. Pooled plasma samples were evaluated for antibody titers against purified LPS from designated types of bacteria by ELISA. Anti-LPS titers in pooled plasma from vaccinated mice were compared with anti-LPS titers in pooled plasma from non-immunized mice. Cross-reactive antibody titers reported in Table 2 were at least 4-5 fold above the non-immune background titer.

TABLE 2

| Bacterial | Cross-Reactivity | | |
|---|---|---|---|
| Source of LPS | E1 | E2 | E3 |
| E. coli J5 | 32200 | 31000 | 52705 |
| E. coli O111 | 7600 | 4200 | 1900 |
| E. coli O128 | 500 | 500 | ND |
| S. enteritidis | 51800 | 50400 | 108235 |
| S. typhimurium | 3400 | 2100 | 18700 |
| S. flexneri | 5300 | 3800 | 2700 |
| P. aeruginosa | 800 | 600 | ND |

E1, E2, E3 = Experiment 1, 2, & 3.
Non-immune serum was equal to or less than 100
ND = Not Detected The results in Table 2 show that the conjugate vaccine with PS antigen from *E. coil* J5 elicited antibodies that cross-reacted with LPS from a variety of wild-type bacteria that have been implicated as causative agents of sepsis, and indicate that the present vaccine could provide beneficial protection against infection caused by these kinds of bacteria.

EXAMPLE 7

Vaccination with *E. coli* J5 PS Antigen-Carrier Conjugate Protects Mice Against Severe Sepsis A model involving induced LPS-hypersensitivity was used to evaluate protective activity conferred by the present conjugate vaccine. Mice were hypersensitized by intraperitoneal injection of heat-killed *Corynebacterium parvum* (C. Galanos et al., *Immunobiol.*, 187, 349 (1993)). Six days after this treatment, the animals were challenged. with 10 ng LPS from *S. enteritidis*. Body temperatures were measured 2 and 6 hours after challenge.

Figure 5:
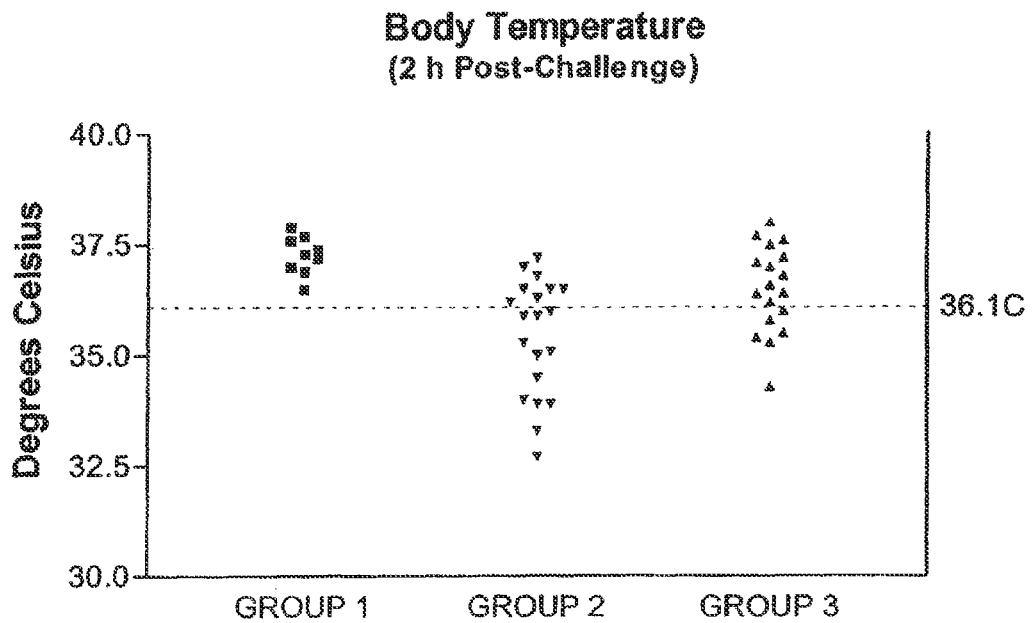
FIGS. 5 and 6 summarize the ability of the present conjugate vaccine to inhibit hypothermia in experimentally induced sepsis in mice.
Figure 6:
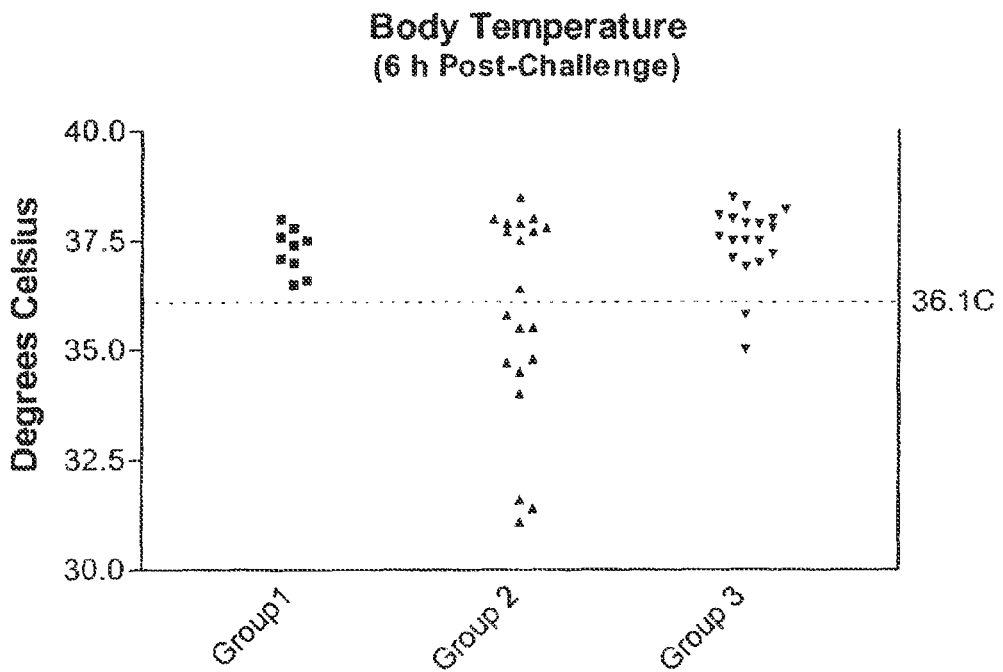

The data in FIGS. 5-6 is derived from two non-vaccinated control groups of mice (Groups 1 and 2) and one experimental group (Group 3). Group 1 was sensitized with *C. parvum*, but was not challenged with LPS; and Group 2 was sensitized and challenged. The experimental group (Group 3) contained mice that had been immunized with three, 100 μg doses of conjugate vaccine containing PS antigen from *E. coli* J5.

In the experiments summarized in FIGS. 5-6, Group 3 mice were sensitized and challenged in the same manner as Group 2. The experiment was scheduled such that Group 3 mice received *C. parvum* sensitization 40 days after tertiary immunization, and they were challenged with LPS 46 days after this immunization. Body temperatures of mice from all groups were measured 2 and 6 hours post-challenge with LPS (FIGS. 5 and 6, respectively).

The results shown in FIG. 5 with Group 1 showed that *C. parvum* treated mice, which were not challenged with LPS, had body temperatures ranging from 36.5 to 38° C., and this temperature range was retained over the course of the observation period (FIG. 6). In contrast, the body temperature range for Group 2 mice at 2 hours post-challenge was 32.7-37.2° C., and about 70% of the mice had body temperatures lower than the minimum temperature observed in Group 1 mice. As shown in FIG. 6, at 6 hours post-challenge about 55% of the mice in Group 2 had body temperatures less than the 36.5° C. minimum temperature of Group 1, and the remainder of Group 2 had temperatures in the range of 37.5 to 38.5° C.

In contrast, the vaccinated group of mice (Group 3), at 2 hours post-challenge, had body temperatures ranging from 34.3 to 38° C., with 47% having temperatures less than the 36.5° C. minimum of Group 1. At 6 hours post-challenge only 2 out of the 19 vaccinated mice (11%) had body temperatures less than 36.5° C., and the remainder had temperatures ranging from 36.9 to 38.5° C.

The body temperature range for normal untreated mice was observed to be 36.1 to 37.1° C., with a mean temperature of 36.7° C. (data not shown). This is similar to the mean, normal body temperature obtained by others (A. Romanovsky et al., *Am. J. Physiol.*, 270, R693 (1996)). Accordingly, for the purpose of evaluating results in FIGS. 5-6, a body temperature above 37.1° C. was considered to be hyperthermic, and a body temperature less than 36.1° C. was considered to be hypothermic. From this perspective, the following conclusions were drawn from the results in FIGS. 5-6: a) about half of the non-vaccinated, hypersensitized mice that were not challenged with LPS (Group 1), had body temperatures in the range of normal mice, and the remainder were modestly hyperthermic; b) most non-vaccinated, hypersensitized mice, that were challenged with LPS, were hypothermic 2 hours post-challenge, and hypothermia persisted in about half of the mice at 6 hours post-challenge; and c) about one-third of the vaccinated, hypersensitized mice were hyperthermic at 2 hours post-challenge, but hypothermia persisted in only 2 out of 19 mice at 6 hours post-challenge.

Prior to the experiment summarized in FIGS. 5-6, the threshold lethal dose of *S. enteritidis* in non-vaccinated, hypersensitized mice was found to be about 20 ng. Accordingly, the 10 ng LPS challenge dose used for the experiment described above was close to the threshold lethal dose for non-vaccinated mice. In small rodents such as mice and rats, persistent hypothermia is a symptom of severe sepsis, and transient hypothermia is a symptom of mild sepsis. See, e.g., R. Blanque et al., *Gen. Pharmacol.*, 27, 973 (1996); T. P. Clemmer et al., *Crit. Care Med.*, 20, 1395 (1992). Accordingly, the results in FIGS. 5-6 support the conclusion that the 10 ng LPS challenge dose caused much more severe sepsis in control mice than in mice immunized with the embodied conjugate vaccine.

In addition to providing protection against sepsis, the embodied conjugate vaccine can also provide protection against other infectious complications. For example, the vaccine can provide protection against infections by *S. enteritidis* that occur in patients with lupus erythematosus and patients with sickle cell disease, and it may also provide protection against gastroenteritis and enteric fever caused by this bacterium. Further, the embodied vaccine can provide protection against urinary tract infections caused by uropathogenic strains of *E. coil*. See, e.g., S. Abramson et al., *Arthritis Rheum.*, 28, 75 (1985); J. R. Wright et al., *J. Pediar.*, 130, 334 (1997); J. L. Taylor et al., *J. Infect. Dis.*, 167, 781 (1993); *MMWR Morb. Weekly Rep.*, 49, 73 (2000). Also, the methods disclosed herein provide a general approach to produce conjugate vaccines that contain other kinds of LPS polysaccharides, and these vaccines could be used alone or in combination to provide prophylactic protection against a wide range of complications and infectious diseases caused by gram-negative bacteria. These include dysentery and diarrhea caused by various species and/or strains of *Shigella, Escherichia coli, Vibrio cholerae, Campylobacter*, and *Yersinia*; meningitis caused by *Haemophilus influenzae* and *Neisseria meningitidis*; enteric fever caused by typhoidal and non-typhoidal *Salmonella*; otitis media caused by *Haemophilus influenzae* and *Moraxella catarrhalis*; respiratory infections caused by species of *Pseudomonas, Moraxella* and *Haemo-*

*philius*; trachoma and sexually transmitted diseases caused by *Chlamydia* species; tularemia caused by *Franciscella tularensis*; brucellosis caused by *Brucella* species, and plague caused by *Yersinia pestis*. See, e.g., J. B. Robbins et al., *Clin. Infect. Dis* 15, 346-61 (1992); D. Cohen et al., *Lancet*, 349, 155-9 (1997); S. Ashkenazi et al., *J. Infect. Dis.*, 179, 1565-8 (1999); E. Konadu et al., *Infect. Immun.*, 62, 5048-54 (1994); R. K. Gupta et al., *Infect. Immun.*, 63, 2805-10 (1995); Z. Kossaczka et al., *Infect. Immun.*, 68, 5037-43 (2000); H. J. Jennings et al., *Infect. Immun.*, 43, 407-12 (1984); J. S. Plested et al., *Infect. Immun.*, 67, 5417-26 (1999); E. Y. Konadu et al., *Infect. Immun.*, 68, 1529-34 (2000); J. Sun et al., *Vaccine*, 18, 1264-72 (2000); W. Hu, *Infect. Immun.*, 68, 4980-85 (2000); and S. J. Cryz et al., *Behring Inst. Mitt.*, 98, 345-9 (1997).

EXAMPLE 8

Ability of Proteinase 1-Based Carrier Vaccine to Potentiate Immunogenic and Immune Memory Response to PS-Antigen in Non-Adjuvantized Vaccines in Saline Using methods described in Examples 1-4, conjugate vaccines were prepared that contained PS-antigens from bacteria that included *E. coli*, *P. aeruginosa*, *S. flexneri*, and *N. meningitidis*. The conjugate vaccines were formulated in saline (0.9% NaCl) and administered to mice by subcutaneous injections. Vaccines were tested in groups of 10 mice with each mouse in a group receiving a primary and two booster doses of vaccine. Boosters were generally administered at 2-3 week intervals following primary injections.

Tables 3-7 present ELISA titers equal to the inverse of the dilutions giving OD (450 nm) readings of 2-fold that of background. Solid-phase antigens for the ELISA assays were either purified species of native LPS, whole bacteria, or PS antigen hydrazide derivatives prepared as described in Example 2. LPS antigens and whole bacteria were non-covalently bound to Immulon HB4 or HB2 96 plates; whereas, PS antigen hydrazides were covalently bonded to ####### Corning DNA-Bind plates.

Table 3 shows the dose response for the anti-J5 PS vaccine after secondary and tertiary injections. There is a clear dose response after both the secondary and tertiary vaccination for the J5 PS conjugate vaccine. Based on the ELISA measurements, the saline-only vaccine showed higher memory amplification after tertiary injection than did the oil-in-water vaccines. The 8 µg post-tertiary titer is higher than any of the oil-in-water vaccines' tertiary titers. The oil-in-water vaccinations had doses of 100, 50, and 25 µg. Thus, the saline-only vaccine shows greater immune activity overall than does the oil-in-water vaccine.

TABLE 3

ELISA Response of Non-adjuvantized J5PS Vaccine Against J5-LPS

| Vaccination | Dose in µg | Anti J5 Titer |
|---|---|---|
| Secondary | 8 | 22,000 (100%) |
|  | 4 | 7,700 (35%) |
|  | 2 | 5,800 (26%) |
|  | 1 | 2,600 (12%) |
| Tertiary | 8 | 88,000 (100%) |
|  | 4 | 38,000 (43%) |
|  | 2 | 17,000 (20%) |
|  | 1 | 5,200 (6%) |

Table 4 presents limited cross-reactivity data for the J5PS vaccine utilizing LPS from its parental *E. coli* bacterial strain, a related bacteria, *Salmonella enteriditis*, and a more distant Gram-negative bacteria, *P. aeruginosa*. The J5 PS conjugate vaccine elicited antibodies that cross-react to a significant extent with the LPS from all three bacterial strains. Similar to the early vaccines, above, the non-adjuvantized vaccine shows the highest cross-reactive response to the *S. enteriditis* LPS.

TABLE 4

ELISA Response of Non-adjuvantized J5PS Vaccine Against Heterologous-LPS's

|  | Titer | % of Homologous[a] |
|---|---|---|
| *Salmonella enteriditis* | 86,000 | 98% |
| *Escherichia. coli* O111 | 12,000 | 14% |
| *Pseudomonas aeruginosa* O10 | 1,000 | 1.1% |

[a]Homologous titer determined with J5-LPS as antigen, = 88,000 (see Table 3, above).

Table 5 presents the dose-response data for antibodies elicited by the anti Pa3 PS vaccine. Since no homologous LPS for this vaccine is available, the ELISA assay used whole bacteria as antigen. Qualitatively these data are similar for that seen for the J5 PS vaccine, except there is less evidence of dose response after the secondary injection. There is, however, substantial evidence of memory amplification occurring after the tertiary injection, as well as evidence of an obvious dose response.

TABLE 5

ELISA Response of Non-adjuvantized Pa3PS Vaccine Against Pa3 Whole Bacteria

| Vaccination | Dose in µg | Anti Pa3 Titer |
|---|---|---|
| Secondary | 8 | 3000 |
|  | 4 | 3000 |
|  | 2 | 3000 |
|  | 1 | 300 |
| Tertiary | 8 | 44,000 |
|  | 4 | 10,000 |
|  | 2 | 6,000 |
|  | 1 | 700 |

Only limited data is available for the cross-reactivity of the Pa3 PS vaccine. Unlike the J5 PS vaccine, the Pa3 PS vaccine elicits antibodies that cross-react well with its wild-type parent bacteria, 41% vs. 14% for the J5 PS vaccine. The Pa3 PS conjugate vaccine cross-reacted to 14% with J5 whole bacteria.

Table 6 shows immunogenicity data for a conjugate vaccine containing PS antigen isolated from *S. flexneri* 2a, substrain BS103. The PS fraction used for this vaccine contained an average of one O-antigen repeat unit per molecule. Each vaccine dose was formulated in saline and administered to a group of 10 mice. Mice in all groups were given primary and two booster injections at each respective vaccine dose level. Titers reflect average values within each group of mice as determined from analyses of pooled sera from each group. Cross-reactivity studies indicated that antibodies elicited by this vaccine were broadly cross-reactive against LPS purified from most serogroups of *S. flexneri* and also with LPS purified from *S. sonnei* and *S. dysenteriae* 1.

TABLE 6

ELISA Titers of anti-LPS Antibodies from Mice Immunized with Conjugate Vaccines Containing PS Antigens from *S. flexneri*

| Vaccine | Dose in μg | Anti-LPS Titer | Anti-PS-Hz Titer |
|---|---|---|---|
| *S. flexneri* 2a | 8 | 40,000 | 68,000 |
|  | 4 | 41,000 | 26,000 |
|  | 2 | 19,000 | 11,000 |
|  | 1 | 20,000 | 10,000 |

Table 7 shows immunogenicity data for a conjugate vaccine containing PS antigen isolated from the SynX-knockout mutant of *N. meningitidis*, strain 9162. Similar to other experiments, each vaccine dose was formulated in saline and administered to a group of 10 mice. Mice in all groups were given primary and two booster injections at each respective vaccine dose level. Titers reflect average values within each group of mice as determined from analyses of pooled sera from each group. Additional studies indicated that antibodies elicited by this vaccine had bactericidal activity against the homologous strain of *N. meningitidis* (strain 9162).

TABLE 7

ELISA Titers of anti-LPS Antibodies from Mice Immunized with Conjugate Vaccines Containing PS Antigens from *N. meningitidis*.

| Vaccine | Dose in μg | Anti-PS-Hz Titer |
|---|---|---|
| *N. meningitidis* | 32 | 118,000 |
|  | 16 | 80,000 |
|  | 8 | 68,000 |
|  | 4 | 34,000 |

These vaccines each prepared similarly using the cellular slime mold, *D. discoideum*, to provide both PS antigen and carrier protein provide further evidence of the applicability of the core techniques presented in this patent and its examples, to the preparation of low-cost effective vaccines from a wide-variety of gram-negative bacteria. Even though these vaccines use only small delipidated LPS carbohydrate haptens, when linked to the carrier protein, Proteinase 1 in the conjugate vaccine, the vaccines elicited significant immune and memory response in mice.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A biologically detoxified lipopolysaccharide (LPS) of *Pseudomonas aeruginosa* comprising a glucosamine disaccharide backbone of lipid A and its polysaccharide including a non-reducing terminal KDO moiety and at least one ethanolamine diphosphate group or at least one ethanolamine monophosphate group, wherein the disaccharide backbone of lipid A does not comprise ester-linked and amide-linked fatty acids and wherein the detoxified LPS is obtained by growing *Dictyostelium discoideum* on *Pseudomonas aeruginosa* under conditions that deacylate LPS of said *Pseudomonas aeruginosa* by cleavage of ester-linked and amide-linked fatty acids.

2. The biologically detoxified LPS of claim 1, wherein carbon-1 at the reducing end of the glucosamine disaccharide backbone lacking the ester-linked and amide-linked fatty acids, is either —OCH—OH or —CHO.

3. The biologically detoxified LPS of claim 2, wherein the carbon-1 at the reducing end of the glucosamine disaccharide backbone lacking the ester-linked and amide-linked fatty acids is substituted with a moiety having a hydrazide (—C(O)NHNH2) functional group.

4. An immunogenic composition comprising the biologically detoxified LPS of claim 2, wherein the detoxified LPS is covalently linked to a carrier protein.

5. An immunogenic composition comprising the biologically detoxified LPS of claim 3, wherein the detoxified LPS is covalently linked to a carrier protein.

6. The immunogenic composition of claim 4, wherein the carrier protein is other than Proteinase 1.

7. The immunogenic composition of claim 5, wherein the carrier protein is other than Proteinase 1.

* * * * *